(12) United States Patent
Miller et al.

(10) Patent No.: US 7,709,496 B2
(45) Date of Patent: May 4, 2010

(54) ANTIBACTERIAL AGENTS

(75) Inventors: William Henry Miller, Collegeville, PA (US); Alan T. Price, Collegeville, PA (US)

(73) Assignee: Glaxo Group Limited, Brentford, Middlesex (GB)

( * ) Notice: Subject to any disclaimer, the term of this patent is extended or adjusted under 35 U.S.C. 154(b) by 0 days.

(21) Appl. No.: 12/296,119

(22) PCT Filed: Apr. 5, 2007

(86) PCT No.: PCT/US2007/066018

§ 371 (c)(1),
(2), (4) Date: Oct. 6, 2008

(87) PCT Pub. No.: WO2007/118130

PCT Pub. Date: Oct. 18, 2007

(65) Prior Publication Data

US 2009/0054418 A1  Feb. 26, 2009

Related U.S. Application Data

(60) Provisional application No. 60/744,348, filed on Apr. 6, 2006.

(51) Int. Cl.
*C07D 491/04* (2006.01)
*C07D 498/04* (2006.01)
*A61K 31/436* (2006.01)
*A61K 31/542* (2006.01)

(52) U.S. Cl. ..................... 514/300; 546/122

(58) Field of Classification Search ............. 546/122; 514/300
See application file for complete search history.

(56) References Cited

U.S. PATENT DOCUMENTS

| | | | |
|---|---|---|---|
| 2003/0232804 A1 | 12/2003 | Pinto et al. | 514/211.09 |
| 2004/0067996 A1 | 4/2004 | Sheppeck | 514/389 |
| 2006/0058287 A1 | 3/2006 | Axten et al. | 514/224.2 |
| 2006/0183739 A1 | 8/2006 | Tsaklakidis et al. | 544/106 |
| 2006/0189604 A1 | 8/2006 | Axten et al. | 514/224.2 |

FOREIGN PATENT DOCUMENTS

| EP | 373891 | 12/1989 |
|---|---|---|
| EP | 0559285 | 3/1993 |
| WO | WO 97/17957 | 5/1997 |
| WO | WO 99/37635 | 7/1999 |
| WO | WO 99/65867 | 12/1999 |
| WO | WO 00/21948 | 4/2000 |
| WO | WO 00/24725 | 5/2000 |
| WO | WO 00/43383 | 7/2000 |
| WO | WO 00/78748 | 12/2000 |
| WO | WO 01/07432 | 2/2001 |
| WO | WO 01/07436 | 2/2001 |
| WO | WO 01/14333 | 3/2001 |
| WO | WO 01/70734 | 9/2001 |
| WO | WO 02/08224 | 1/2002 |
| WO | WO 02/24684 | 3/2002 |
| WO | WO 02/50036 | 6/2002 |
| WO | WO 02/50040 | 6/2002 |
| WO | WO 02/50061 | 6/2002 |
| WO | WO 02/056882 | 7/2002 |
| WO | WO 02/096907 | 12/2002 |
| WO | WO 03/010138 | 2/2003 |
| WO | WO 03/047520 | 6/2003 |
| WO | WO 03/048081 | 6/2003 |
| WO | WO 03/048158 | 6/2003 |
| WO | WO 03/062234 | 7/2003 |
| WO | WO 03/064421 | 8/2003 |
| WO | WO 03/064431 | 8/2003 |
| WO | WO 03/087098 | 10/2003 |
| WO | WO 2004/002490 | 1/2004 |
| WO | WO 2004/002992 | 1/2004 |
| WO | WO 2004/014361 | 2/2004 |
| WO | WO 2004/041210 | 5/2004 |
| WO | WO 2004/058144 | 7/2004 |
| WO | WO 2004/083174 | 9/2004 |
| WO | WO 2004/087145 | 10/2004 |
| WO | WO 2004/087646 | 10/2004 |
| WO | WO 2004/096982 | 11/2004 |
| WO | WO 2006/002047 | 1/2006 |
| WO | WO 2006/010040 | 1/2006 |
| WO | WO 2006/012396 | 2/2006 |
| WO | WO 2006/014580 | 2/2006 |
| WO | WO 2006/017326 | 2/2006 |
| WO | WO 2006/017468 | 2/2006 |
| WO | WO 2006/020561 | 2/2006 |

OTHER PUBLICATIONS

Snyder et al., PubMed Abstract (J. Med. Liban 48(4): 208-214, Jul.-Aug. 2000.*

Sukdolak, et al. Synthesis and Antimicrobial Activity of New N-[4-(4-Hydroxy-2-oxo-2H-chromen-3-yl)thiazol-2-yl]benzenesulfonamides. Chem. Pap. 2005, vol. 59(1)pp. 37-40.*

* cited by examiner

*Primary Examiner*—Kahsay T Habte
(74) *Attorney, Agent, or Firm*—Reid S. Willis; John Lemanowicz

(57) ABSTRACT

2H-chromen-2-one derivatives useful in the treatment of bacterial infections in mammals, particularly humans, are disclosed herein.

17 Claims, No Drawings

ANTIBACTERIAL AGENTS

This application is a 371 of International Application No. PCT/US2007/066018, filed 5 Apr. 2007, which claims the benefit of U.S. Provisional Application No. 60/744,348, filed 6 Apr. 2006.

FIELD OF THE INVENTION

This invention relates to novel compounds, compositions containing them and their use as antibacterials.

BACKGROUND OF THE INVENTION

The emergence of pathogens resistant to known antibiotic therapy is becoming a serious global healthcare problem (Chu, et al., (1996) *J. Med. Chem.*, 39: 3853-3874). Thus, there is a need to discover new broad spectrum antibiotics useful in combating multidrug-resistant organisms. Importantly, it has now been discovered that certain compounds have antibacterial activity, and, therefore, may be useful for the treatment of bacterial infections in mammals, particularly in humans.

SUMMARY OF THE INVENTION

This invention comprises compounds of the formula (I), as described hereinafter, which are useful in the treatment of bacterial infections. This invention also comprises a pharmaceutical composition comprising a compound according to formula (I) and a pharmaceutically acceptable carrier. This invention also comprises processes for the preparation of compounds of formula (I), as well as processes for the preparation of intermediates useful in the synthesis of compounds of formula (I). This invention also comprises a method of treating bacterial infections in mammals, particularly in humans.

DETAILED DESCRIPTION OF THE INVENTION

In some embodiments, this invention provides a compound of formula (I):

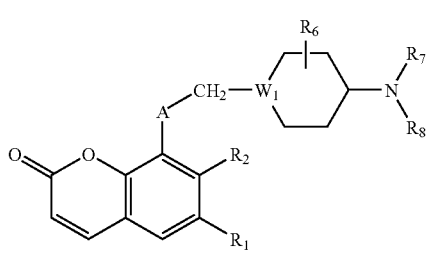

wherein:
$R_1$ is hydrogen; fluorine; or chlorine;
$R_2$ is hydrogen; fluorine; chlorine; or CN;
A is $CR_3R_4$;
$R_3$ is hydrogen;
$R_4$ is hydrogen or hydroxyl;
$W_1$ is $CR_5$ or N;
$R_5$ is hydrogen or hydroxyl;
$R_6$ is hydrogen, $(C_{1-6})$alkyl; fluorine; chlorine; $NR^{1a}R^{1a'}$; $(C_{1-6})$alkyl$NR^{1a}R^{1a'}$; $(C_{1-6})$alkoxy; $(C_{1-6})$alkyl$(C_{1-6})$alkoxy; $(C_{1-6})$hydroxyalkyl; hydroxyl; aryl; heteroaryl; heterocyclyl; $(C_{1-6})$aralkyl; thiol; $(C_{1-6})$alkylthio; $C(=O)NR^{1a}R^{1a'}$; $(C_{1-6})$alkylC$(=O)NR^{1a}R^{1a'}$; $C(=O)R^{1b}$; $(C_{1-6})$alkyl$C(=O)R^{1b}$; $CO_2R^{1b}$; or $(C_{1-6})$alkyl$CO_2R^{1b}$;

each $R^{1a}$ and $R^{1a'}$ are independently hydrogen; acyl; $(C_{1-6})$alkyl; aryl; heteroaryl; or together with the nitrogen they are attached form an aziridine, azetidine, pyrrolidine, piperidine or hexamethyleneimine ring (wherein said aziridine, azetidine, pyrrolidine, piperidine or hexamethyleneimine ring is optionally substituted with 1 to 3 substitutents selected from halogen, $(C_{1-6})$alkyl, hydroxyl or aryl);

each $R^{1b}$ is independently hydrogen; $(C_{1-6})$alkyl; aryl; or heteroaryl;

$R_7$ is hydrogen; $(C_{1-6})$alkyl$(C_{1-6})$alkoxy; $(C_{1-6})$alkyl$NR^{1a}R^{1a'}$; or $(C_{1-6})$alkyl;

$R_8$ is a group —U—$R_9$ where $R_9$ is a substituted or unsubstituted bicyclic carbocyclic or heterocyclic ring system (A):

containing up to four heteroatoms in each ring in which at least one of rings (a) and (b) is aromatic;

$X^1$ is C or N when part of an aromatic ring or $CR_{10}$ when part of a non aromatic ring;

$X^2$ is N, $NR_{11}$, O, $S(O)_x$, CO or $CR_{10}$ when part of an aromatic or non-aromatic ring or may in addition be $CR_{12}R_{13}$ when part of a non aromatic ring;

$X^3$ and $X^5$ are independently N or C;

$Y^1$ is a 0 to 4 atom linker group each atom of which is independently selected from N, $NR_{11}$, O, $S(O)_x$, CO and $CR_{10}$ when part of an aromatic or non-aromatic ring or may additionally be $CR_{12}R_{13}$ when part of a non aromatic ring, $Y^2$ is a 2 to 6 atom linker group, each atom of $Y^2$ being independently selected from N, $NR_{11}$, O, $S(O)_x$, CO and $CR_{10}$ when part of an aromatic or non-aromatic ring or may additionally be $CR_{12}R_{13}$ when part of a non aromatic ring;

$R_{10}$, $R_{12}$ and $R_{13}$ are at each occurrence independently selected from: H; $(C_{1-4})$alkylthio; halo; $(C_{1-4})$alkyl; $(C_{2-4})$alkenyl; hydroxy; hydroxy$(C_{1-4})$alkyl; mercapto$(C_{1-4})$alkyl; $(C_{1-4})$alkoxy; trifluoromethoxy; nitro; cyano; carboxy; amino or aminocarbonyl unsubstituted or substituted by $(C_{1-4})$alkyl;

$R_{11}$ is at each occurrence independently hydrogen; trifluoromethyl; $(C_{1-4})$alkyl unsubstituted or substituted by hydroxy, carboxy, $(C_{1-4})$alkoxy, $(C_{1-6})$alkylthio, halo or trifluoromethyl; $(C_{2-4})$alkenyl; or aminocarbonyl wherein the amino group is optionally substituted with $(C_{1-4})$alkyl;

each x is independently 0, 1 or 2;

U is $C(=O)$; $SO_2$; or $CR_{14}R_{15}$; and $R_{14}$ and $R_{15}$ are independently selected from H; aryl; heteroaryl; $(C_{1-6})$alkyl; $(C_{1-6})$alkyl substituted by $(C_{1-6})$alkoxy, hydroxy, amino, piperidyl, piperazinyl, morpholino, guanidino, or amidino, any of which is substituted or N-substituted by one or two hydrogen, aryl, heteroaryl, halogen, cyano, $CF_3$, $(C_{1-6})$alkyl, acyl, $(C_{1-6})$alkylsulphonyl, arylsulphonyl, hydroxy, $(C_{1-6})$alkylthio, heterocyclylthio, heterocyclyloxy, arylthio, aryloxy, acylthio, acyloxy, or $(C_{1-6})$alkylsulphonyloxy, so long as the substitution does not lead to an unstable compound; ($C_{1-6}$)alkoxy-substituted ($C_{1-6}$)alkyl; hydroxy-substituted($C_{1-6}$)alkyl; amino-substituted ($C_{1-6}$)alkyl, which is N-substituted by one or two ($C_{1-6}$) alkyl, acyl, ($C_{1-6}$)alkylsulphonyl, or arylsulphonyl; ($C_{1-6}$)alkylcarbonyl; ($C_{2-6}$)alkenylcarbonyl; ($C_{1-6}$) alkoxycarbonyl; $CO_2H$; or $CF_3$;

or a pharmaceutically acceptable derivative (e.g., salts, solvates, N-oxides) thereof.

In some embodiments, this invention describes a compound according to formula (I), wherein $R_1$ is hydrogen.

In some embodiments, this invention describes a compound according to formula (I), wherein $R_1$ is chlorine.

In some embodiments, this invention describes a compound according to formula (I), wherein $R_2$ is hydrogen or fluorine.

In some embodiments, this invention describes a compound according to formula (I), wherein A is $CH_2$.

In some embodiments, this invention describes a compound according to formula (I), wherein $W_1$ is $CR_5$.

In some embodiments, this invention describes a compound according to formula (I), wherein $W_1$ is N.

In some embodiments, this invention describes a compound according to formula (I), wherein $R_5$ is hydroxyl.

In some embodiments, this invention describes a compound according to formula (I), wherein $R_6$ is hydrogen.

In some embodiments, this invention describes a compound according to formula (I), wherein the compound has one or two, especially one, $R_6$ groups other than hydrogen. In some embodiments, such $R_6$ groups are independently hydroxyl or fluorine.

In some embodiments, this invention describes a compound according to formula (I), wherein $R_7$ is hydrogen.

In some embodiments, this invention describes a compound according to formula (I), wherein U is $CH_2$.

In some embodiments, this invention describes a compound according to formula (I), wherein $R_9$ is 4H-Pyrido[3,2-b][1,4]thiazin-3-oxo-6-yl; 4H-Pyrido[3,2-b][1,4]oxazin-3-oxo-6-yl; or 2,3-Dihydro-[1,4]dioxino[2,3-c]-pyridin-6-yl.

In some embodiments, this invention describes a compound according to formula (I), wherein the compound is 6-[({cis-4-[2-(6-chloro-2-oxo-2H-chromen-8-yl)ethyl]-4-hydroxycyclohexyl}amino)methyl]-2H-pyrido[3,2-b][1,4]oxazin-3(4H)-one; chloro-8-(2-{cis-4-[(2,3-dihydro[1,4]dioxino[2,3-c]pyridin-7-ylmethyl)amino]-1-hydroxycyclohexyl}ethyl)-2H-chromen-2-one; 6-[({cis-4-[2-(6-chloro-2-oxo-2H-chromen-8-yl)ethyl]-4-hydroxycyclohexyl}amino)methyl]-2H-pyrido[3,2-b][1,4]thiazin-3(4H)-one; 6-[({cis-4-hydroxy-4-[2-(2-oxo-2H-chromen-8-yl)ethyl]cyclohexyl}amino)methyl]-2H-pyrido[3,2-b][1,4]oxazin-3(4H)-one; 8-(2-{cis-4-[(2,3-dihydro[1,4]dioxino[2,3-c]pyridin-7-ylmethyl)amino]-1-hydroxycyclohexyl}ethyl)-2H-chromen-2-one; 6-[({1-[2-(2-oxo-2H-chromen-8-yl)ethyl]-4-piperidinyl}amino)methyl]-2H-pyrido[3,2-b][1,4]thiazin-3(4H)-one; or 8-(2-{4-[(2,3-dihydro[1,4]dioxino[2,3-c]pyridin-7-ylmethyl)amino]-1-piperidinyl}ethyl)-2H-chromen-2-one; or a pharmaceutically acceptable derivative thereof (e.g., a salt or solvate thereof).

In some embodiments, this invention describes a pharmaceutical composition comprising a compound according to formula (I) and a pharmaceutically acceptable carrier.

In some embodiments, this invention describes a method of treating bacterial infections in mammals which comprises administering to a mammal in need thereof an effective amount of a compound according to formula (I).

In some embodiments, this invention describes the use of a compound of formula (I) in the manufacture of a medicament for the treatment of bacterial infections in mammals.

In some embodiments of this invention, the mammal to be treated is a man.

In some embodiments, this invention describes compounds of formula I wherein the (a) and (b) rings of $R_9$ are both aromatic as demonstrated by the following non-limiting examples: 1H-pyrrolo[2,3-b]-pyridin-2-yl, 1H-pyrrolo[3,2-b]-pyridin-2-yl, 3H-imidazo[4,5-b]-pyrid-2-yl, 3H-quinazolin-4-one-2-yl, benzimidazol-2-yl, benzo[1,2,3]-thiadiazol-5-yl, benzo[1,2,5]-oxadiazol-5-yl, benzofur-2-yl, benzothiazol-2-yl, benzo[b]thiophen-2-yl, benzoxazol-2-yl, chromen-4-one-3-yl, imidazo[1,2-a]pyridin-2-yl, imidazo-[1,2-a]-pyrimidin-2-yl, indol-2-yl, indol-6-yl, isoquinolin-3-yl, [1,8]-naphthyridine-3-yl, oxazolo[4,5-b]-pyridin-2-yl, quinolin-2-yl, quinolin-3-yl, quinoxalin-2-yl, indan-2-yl, naphthalen-2-yl, 1,3-dioxo-isoindol-2yl, benzimidazol-2-yl, benzothiophen-2-yl, 1H-benzotriazol-5-yl, 1H-indol-5-yl, 3H-benzooxazol-2-one-6-yl, 3H-benzooxazol-2-thione-6-yl, 3H-benzothiazol-2-one-5-yl, 3H-quinazolin-4-one-2-yl, 3H-quinazolin-4-one-6-yl, 4-oxo-4H-pyrido[1,2-a]pyrimidin-3-yl, benzo[1,2,3]thiadiazol-6-yl, benzo[1,2,5]thiadiazol-5-yl, benzo[1,4]oxazin-2-one-3-yl, benzothiazol-5-yl, benzothiazol-6-yl, cinnolin-3-yl, imidazo[1,2-a]pyridazin-2-yl, imidazo[1,2-b]pyridazin-2-yl, pyrazolo[1,5-a]pyrazin-2-yl, pyrazolo[1,5-a]pyridin-2-yl, pyrazolo[1,5-a]pyrimidin-6-yl, pyrazolo[5,1-c][1,2,4]triazin-3-yl, pyrido[1,2-a]pyrimdin-4-one-2-yl, pyrido[1,2-a]pyrimidin-4-one-3-yl, quinazolin-2-yl, quinoxalin-6-yl, thiazolo[3,2-a]pyrimidin-5-one-7-yl, thiazolo[5,4-b]pyridin-2-yl, thieno[3,2-b]pyridin-6-yl, thiazolo[5,4-b]pyridin-6-yl, 4-oxo-4H-pyrido[1,2-a]pyrimidin-2-yl, 1-oxo-1,2-dihydro-isoquinolin-3-yl, thiazolo[4,5-b]pyridin-5-yl, [1,2,3]thiadiazolo[5,4-b]pyridin-6-yl, 2H-isoquinolin-1-one-3-yl. Thus, suitable $R_9$ groups include:

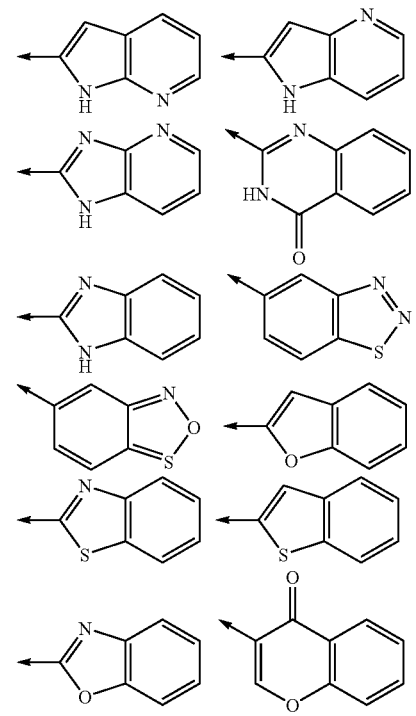

-continued

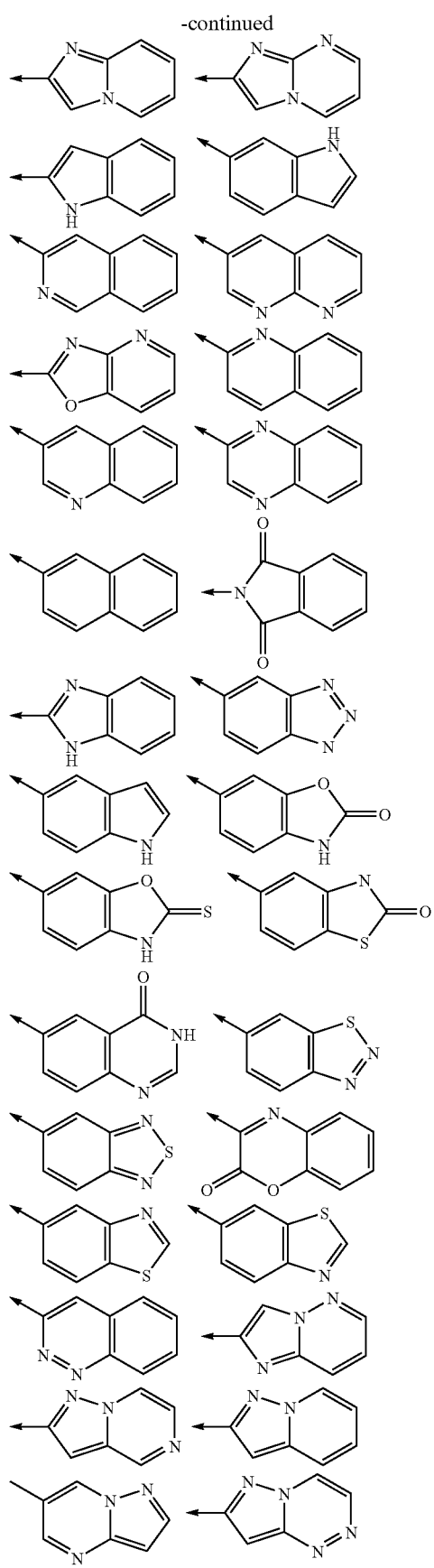

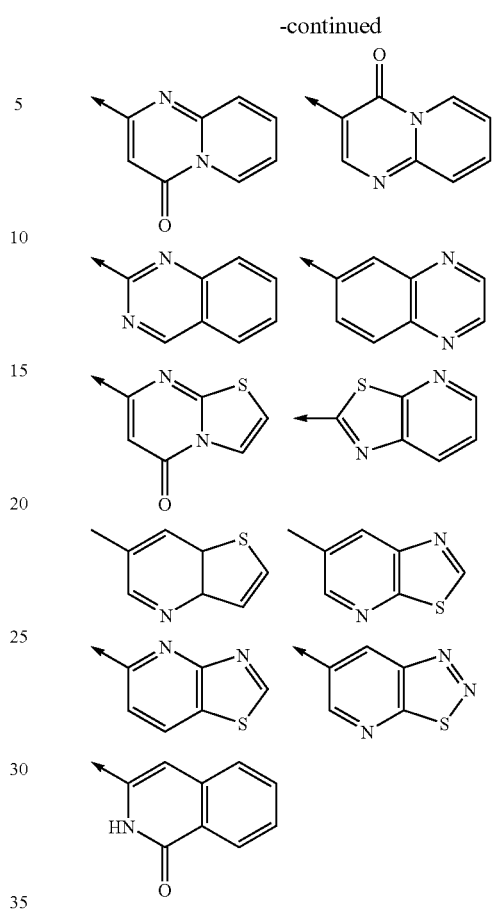

In yet other embodiments, $R_9$ is defined by a non-aromatic (a) ring and aromatic (b) ring as illustrated by the following non-limiting examples: (2S)-2,3-dihydro-1H-indol-2-yl, (2S)-2,3-dihydro-benzo[1,4]dioxine-2-yl, 3-(R,S)-3,4-dihydro-2H-benzo[1,4]thiazin-3-yl, 3-(R)-2,3-dihydro-[1,4]dioxino[2,3-b]pyridin-3-yl, 3-(S)-2,3-dihydro-[1,4]dioxino[2,3-b]pyridin-3-yl, 2,3-dihydro-benzo[1,4]dioxan-2-yl, 3-substituted-3H-quinazolin-4-one-2-yl, 2,3-dihydro-benzo[1,4]dioxan-2-yl, 1-oxo-1,3,4,5-tetrahydrobenzo[c]azepin-2-yl. Thus, suitable $R_9$ groups include:

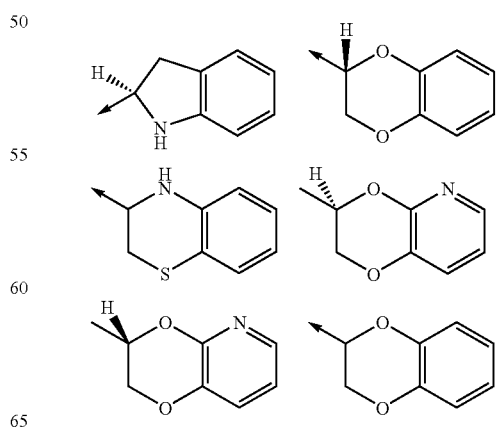

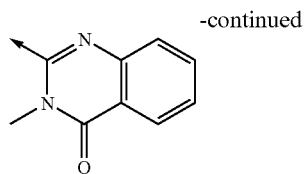

In still other embodiments, $R_9$ is defined by an aromatic (a) ring and a non aromatic (b) ring as illustrated by the following non-limiting examples: 1,1,3-trioxo-1,2,3,4-tetrahydro-1$^{/6}$-benzo[1,4]thiazin-6-yl, benzo[1,3]dioxol-5-yl, 2,3-dihydro-benzo[1,4]dioxin-6-yl, 2-oxo-2,3-dihydro-benzooxazol-6-yl (benzoxazole-2(3H)-one-6-yl); 6-substituted benzoxazole-2 (3H)-one), 4H-benzo[1,4]oxazin-3-one-6-yl (3-oxo-3,4-dihydro-2H-benzo[1,4]oxazin-6-yl), 4H-benzo[1,4]thiazin-3-one-6-yl (3-oxo-3,4-dihydro-2H-benzo[1,4]thiazin-6-yl), 4H-benzo[1,4]oxazin-3-one-7-yl, 4-oxo-2,3,4,5-tetrahydro-benzo[1,5]thiazepine-7-yl, 4-oxo-2,3,4,5-tetrahydro-benzo [b][1,4]thiazepine-7-yl, 5-oxo-2,3-dihydro-5H-thiazolo[3,2-a]pyrimidin-6-yl, benzo[1,3]dioxol-5-yl, 1H-pyrido[2,3-b][1,4]thiazin-2-one-7-yl (2-oxo-2,3-dihydro-1H-pyrido[2,3-b][1,4]thiazin-7-yl), 2-oxo-2,3-dihydro-1H-pyrido[3,4-b][1,4]thiazin-7-yl, 3-oxo-3,4-dihydro-2H-pyrido[3,2-b][1,4]thiazin-6-yl, 2,3-dihydro-[1,4]dioxino[2,3-b]pyridin-6-yl, 2,3-dihydro-[1,4]dioxino[2,3-c]pyridin-7-yl, 2,3-dihydro-[1,4]dioxino[2,3-b]pyridin-7-yl, 6,7-dihydro-[1,4]dioxino[2,3-d]pyrimidin-2-yl, 3-oxo-3,4-dihydro-2H-pyrido[3,2-b][1,4]oxazin-6-yl, 2-oxo-2,3-dihydro-1H-pyrido[3,4-b][1,4]oxazin-7-yl, 2-oxo-2,3-dihydro-1H-pyrido[2,3-b][1,4]oxazin-7-yl, 6-oxo-6,7-dihydro-5H-8-thia-1,2,5-triaza-naphthalen-3-yl (3-substituted 5H-pyridazino[3,4-b][1,4]thiazin-6(7H)-one), 3,4-dihydro-2H-benzo[1,4]oxazin-6-yl, 3-substituted-3H-benzooxazol-2-one-6-yl, 3-substituted-3H-benzooxazole-2-thione-6-yl, 3-substituted-3H-benzothiazol-2-one-6-yl, 2,3-dihydro-1H-pyrido[2,3-b][1,4]thiazin-7-yl, 3,4-dihydro-2H-benzo[1,4]thiazin-6-yl, 3,4-dihydro-1H-quinolin-2-one-7-yl, 3,4-dihydro-1H-quinoxalin-2-one-7-yl, 6,7-dihydro-4H-pyrazolo[1,5-a]pyrimidin-5-one-2-yl, 5,6,7,8-tetrahydro-[1,8]naphthyridin-2-yl (1,2,3,4-tetrahydro-[1,8]naphthyridin-7-yl), 2-oxo-3,4-dihydro-1H-[1,8]naphthyridin-6-yl, 3,4-dihydro-2H-pyrido[3,2-b][1,4]thiazin-6-yl, [1,3]oxathiolo[5,4-c]pyridin-6-yl, 3,4-dihydro-2H-pyrano[2,3-c]pyridine-6-yl, 2,3-dihydro[1,4]oxathiino[2,3-c]pyridine-7-yl. Thus, suitable $R_9$ groups include:

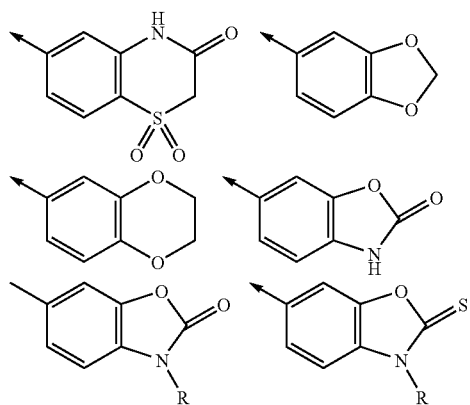

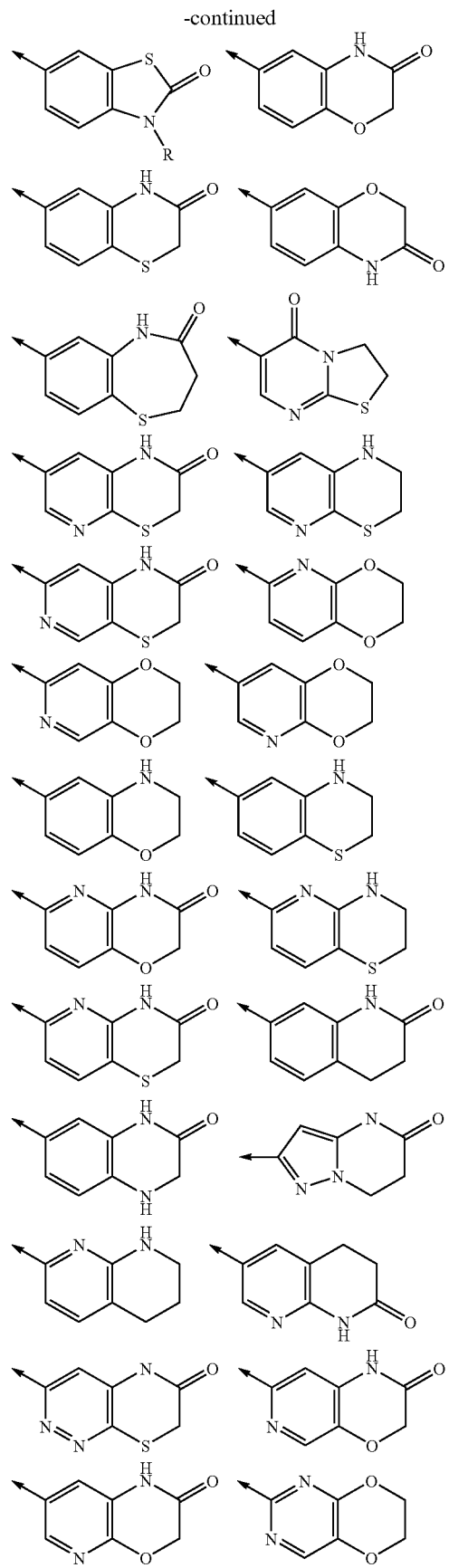

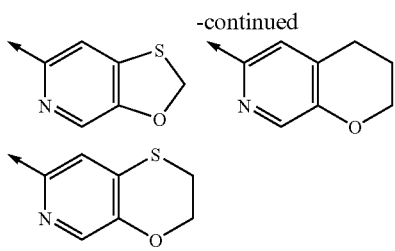

In some embodiments R₉ is selected from [1,2,3]thiadiazolo[5,4-b]pyridin-6-yl; 1H-pyrrolo[2,3-b]pyridin-2-yl; 2,3-dihydro-[1,4]dioxino[2,3-b]pyridin-6-yl; 2,3-dihydro-[1,4]dioxino[2,3-b]pyridin-7-yl; 2,3-dihydro-[1,4]dioxino[2,3-c]pyridin-7-yl; 2,3-dihydro-benzo[1,4]dioxin-6-yl; 2-oxo-2,3-dihydro-1H-pyrido[2,3-b][1,4]oxazin-7-yl; 2-oxo-2,3-dihydro-1H-pyrido[2,3-b][1,4]thiazin-7-yl; 3,4-dihydro-2H-benzo[1,4]oxazin-6-yl; 3-methyl-2-oxo-2,3-dihydro-benzooxazol-6-yl (6-substituted 3-methyl-1,3-benzoxazol-2 (3H)-one); 3-oxo-3,4-dihydro-2H-benzo[1,4]oxazin-6-yl; 3-oxo-3,4-dihydro-2H-pyrido[3,2-b][1,4]oxazin-6-yl (6-substituted 2H-pyrido[3,2-b][1,4]oxazin-3(4H)-one); 3-oxo-3,4-dihydro-2H-benzo[1,4]thiazin-6-yl (4H-benzo[1,4]thiazin-3-one-6-yl); 4-oxo-4H-pyrido[1,2-a]pyrimidin-2-yl; 6-nitro-benzo[1,3]dioxol-5-yl; 7-fluoro-3-oxo-3,4-dihydro-2H-benzo[1,4]oxazin-6-yl; 8-hydroxy-1-oxo-1,2-dihydro-isoquinolin-3-yl; 8-hydroxyquinolin-2-yl; benzo[1,2,3]thiadiazol-5-yl; benzo[1,2,5]thiadiazol-5-yl; benzothiazol-5-yl; thiazolo-[5,4-b]pyridin-6-yl; 3-oxo-3,4-dihydro-2H-pyrido[3,2-b][1,4]thiazin-6-yl (6-substituted 2H-pyrido[3,2-b][1,4]thiazin-3(4H)-one); 7-chloro-3-oxo-3,4-dihydro-2H-pyrido[3,2-b][1,4]thiazin-6-yl; 7-chloro-3-oxo-3,4-dihydro-2H-pyrido[3,2-b][1,4]oxazin-6-yl (6-substituted 7-chloro-2H-pyrido[3,2-b][1,4]oxazin-3(4H)-one); 7-fluoro-3-oxo-3,4-dihydro-2H-pyrido[3,2-b][1,4]thiazin-6-yl; 2-oxo-2,3-dihydro-1H-pyrido[3,4-b][1,4]thiazin-7-yl; [1,3]oxathiolo[5,4-c]pyridin-6-yl; 3,4-dihydro-2H-pyrano[2,3-c]pyridine-6-yl; 2,3-dihydro-5-carbonitro-1,4-benzodioxin-7-yl (7-substituted 2,3-dihydro-1,4-benzodioxin-5-carbonitrile); 2,3-dihydro[1,4]oxathiino[2,3-c]pyridine-7-yl; 2,3-dihydro-1-benzofuran-5-yl. Thus, in some embodiments R₉ is selected from:

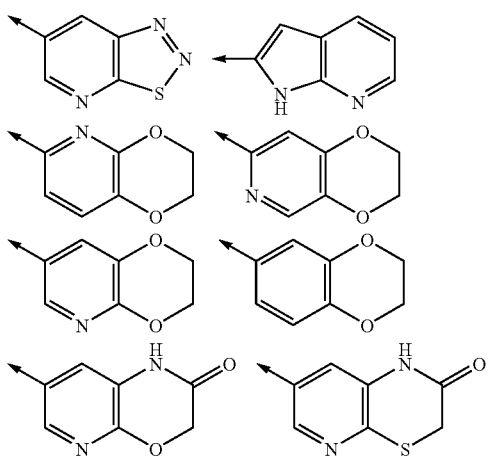

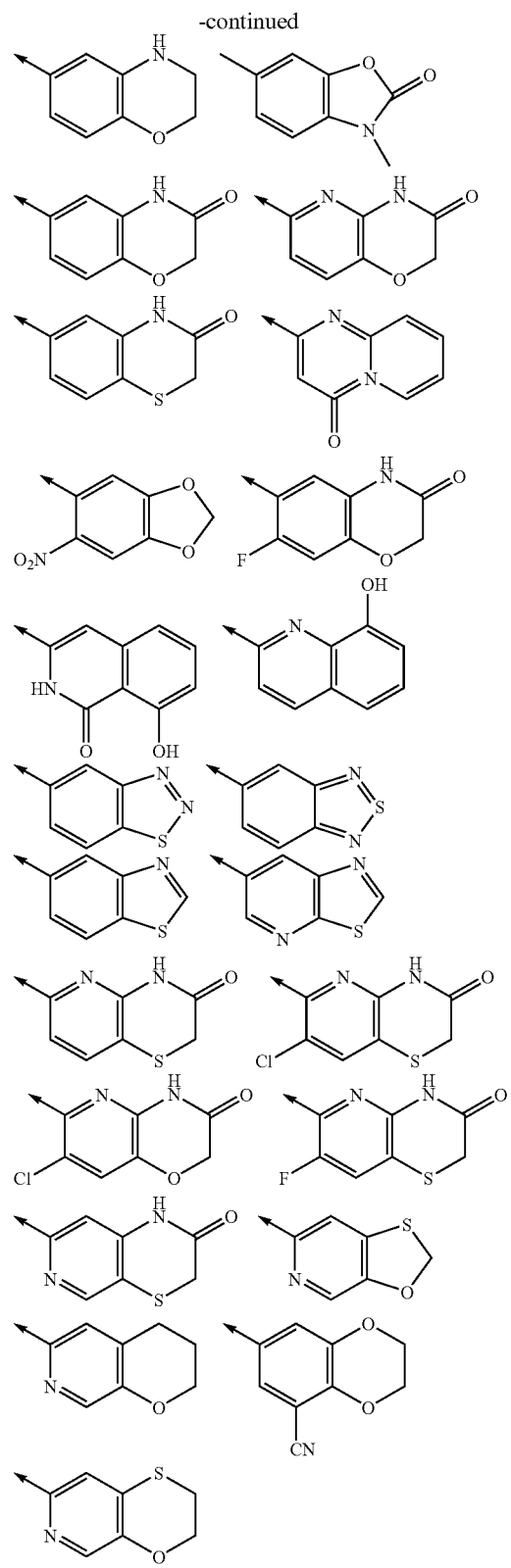

In some embodiments R₉ is selected from 6-substituted 2H-pyrido[3,2-b][1,4]oxazin-3(4H)-one; 2,3-dihydro-[1,4]dioxino[2,3-c]pyridin-7-yl; [1,3]oxathiolo[5,4-c]pyridin-6-yl; 3,4-dihydro-2H-pyrano[2,3-c]pyridine-6-yl; 6-substituted 2H-pyrido[3,2-b][1,4]thiazin-3(4H)-one; and 6-substituted 7-chloro-2H-pyrido[3,2-b][1,4]oxazin-3(4H)-one. Thus in some embodiments $R_9$ is selected from:

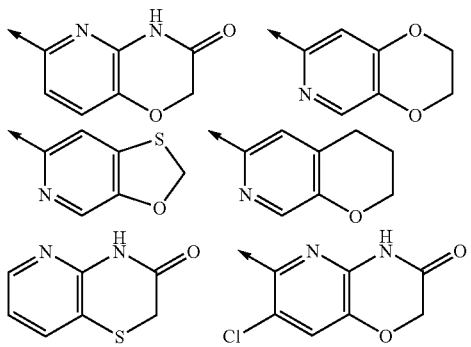

Unless otherwise defined, the term "alkyl" when used alone or when forming part of other groups (such as the 'alkoxy' group) includes substituted or unsubstituted, straight or branched chain alkyl groups containing the specified range of carbon atoms. For example, the term "$(C_{1-6})$alkyl" include methyl, ethyl, propyl, butyl, iso-propyl, sec-butyl, tert-butyl, iso-pentyl, and the like.

The term "alkenyl" means a substituted or unsubstituted alkyl group of the specified range of carbon atoms, wherein one carbon-carbon single bond is replaced by a carbon-carbon double bond. For example, the term "$(C_{2-6})$alkenyl" include ethylene, 1-propene, 2-propene, 1-butene, 2-butene, and isobutene, and the like. Both cis and trans isomers are included.

The term "cycloalkyl" refers to substituted or unsubstituted carbocyclic system of the specified range of carbon atoms, which may contain up to two unsaturated carbon-carbon bonds. For example, the term "$(C_{3-7})$cycloalkyl" include cyclopropyl, cyclobutyl, cyclopentyl, cyclopentenyl, cyclohexyl, cyclohexenyl, and cycloheptyl.

The term "alkoxy" refers to an O-alkyl radical where the alkyl group contains the specified range of carbon atoms and is as defined herein.

The term "alkylalkoxy" refers to an alkylalkoxy radical wherein the alkyl and the alkoxy portion of said radical each contain the specified range of carbon atoms as defined herein.

The term "acyl" refers to a C(=O)alkyl or a C(=O)aryl radical. In some embodiments, the alkyl group contains 13 or less carbons; in some embodiments 10 or less carbon atoms; in some embodiments 6 or less carbon atoms; and is as otherwise defined. Aryl is as defined herein.

The term "alkylsulphonyl" refers to an $SO_2$alkyl radical wherein the alkyl group contains the specified range of carbon atoms and is as defined herein.

The term "alkylthio" refers to an S-alkyl radical, wherein the alkyl group contains the specified range of carbon atoms and is as defined herein.

The term "heterocyclylthio" refers to an S-heterocyclyl radical wherein the heterocyclyl moiety is as defined herein.

The term "aralkyl" refers to an alkyl aryl radical wherein the alkyl group has the specified number range of carbon atoms and the aryl group is as otherwise defined herein.

The term "heterocyclyloxy" refers to an O-heterocyclyl radical wherein heterocyclyl is as defined herein.

The term "arylthio" refers to an S-aryl radical wherein aryl is as defined herein.

The term "aryloxy" refers to an O-aryl radical wherein aryl is as defined herein.

The term "acylthio" refers to a S-acyl radical wherein acyl is as defined herein.

The term "acyloxy" refers to an O-acyl radical wherein acyl is as defined herein.

The term "alkoxycarbonyl" refers to a $CO_2$alkyl radical wherein the alkyl group contains the specified range of carbon atoms and is as defined herein.

The term "alkylsulphonyloxy" refers to an O—$SO_2$alkyl radical wherein the alkyl group contains the specified range of carbon atoms and is as defined herein.

The term "arylsulphonyl" refers to a $SO_2$aryl radical wherein aryl is as herein defined.

The term "arylsulphoxide" refers to a SOaryl radical wherein aryl is as defined herein.

Unless otherwise defined, suitable substituents for any alkyl, alkoxy, alkenyl, and cycloalkyl groups includes up to three substituents selected from the group consisting of hydroxy, halogen, nitro, cyano, carboxy, amino, amidino, sulphonamido, unsubstituted $(C_{1-3})$alkoxy, trifluoromethyl, and acyloxy.

Halo or halogen includes fluoro, chloro, bromo and iodo.

The term "haloalkyl" refers to an alkyl radical containing the specified range of carbon atoms and is as otherwise defined herein, which is further substituted with 1-3 halogen atoms.

The term "haloalkoxy" refers to an alkoxy radical of the specified range and as defined herein, which is further substituted with 1-3 halogen atoms.

The term "hydroxyalkyl" refers to an alkyl group as defined herein, further substituted with a hydroxy group.

Unless otherwise defined, the term "heterocyclic" as used herein includes optionally substituted aromatic and non-aromatic, single and fused, mono- or bicyclic rings suitably containing up to four hetero-atoms in each ring selected from oxygen, nitrogen and sulphur, which rings may be unsubstituted or C-substituted by, for example, up to three groups selected from $(C_{1-4})$alkylthio; halo; $(C_{1-4})$haloalkoxy; $(C_{1-4})$haloalkyl; $(C_{1-4})$alkyl; $(C_{2-4})$alkenyl; hydroxy; hydroxy, $(C_{1-4})$alkyl; $(C_{1-4})$thioalkyl; $(C_{1-4})$alkoxy; nitro; cyano; carboxy; $(C_{1-4})$alkylsulphonyl; $(C_{2-4})$alkenylsulphonyl; or aminosulphonyl wherein the amino group is optionally substituted by $(C_{1-4})$alkyl or $(C_{2-4})$alkenyl.

Each heterocyclic ring suitably has from 3 to 7, preferably 5 or 6, ring atoms. A fused heterocyclic ring system may include carbocyclic rings and need include only one heterocyclic ring.

Compounds within the invention containing a heterocyclyl group may occur in two or more tautometric forms depending on the nature of the heterocyclyl group; all such tautomeric forms are included within the scope of the invention.

Where an amino group forms part of a single or fused non-aromatic heterocyclic ring as defined above suitable optional substituents in such substituted amino groups include hydrogen; trifluoromethyl; $(C_{1-4})$alkyl optionally substituted by hydroxy, $(C_{1-4})$alkoxy, $(C_{1-4})$alkylthio, halo or trifluoromethyl; and $(C_{2-4})$alkenyl.

When used herein the term "aryl", includes optionally substituted phenyl and naphthyl.

Aryl groups may be optionally substituted with up to five, preferably up to three, groups selected from $(C_{1-4})$alkylthio; halo; $(C_{1-4})$haloalkoxy; $(C_{1-4})$haloalkyl; $(C_{1-4})$alkyl; $(C_{2-4})$alkenyl; hydroxy; $(C_{1-4})$hydroxyalkyl; $(C_{1-4})$alkylthio; $(C_{1-4})$alkoxy; nitro; cyano; carboxy; amino or aminocarbonyl optionally substituted by $(C_{1-4})$alkyl; $(C_{1-4})$alkylsulphonyl; $(C_{2-4})$alkenylsulphonyl.

As used herein, the term "pharmaceutically acceptable" means a compound which is suitable for pharmaceutical use. Salts and solvates of compounds of the invention which are suitable for use in medicine are those wherein the counterion or associated solvent is pharmaceutically acceptable. However, salts and solvates having non-pharmaceutically acceptable counterions or associated solvents are within the scope of the present invention, for example, for use as intermediates in the preparation of other compounds of the invention and their pharmaceutically acceptable salts and solvates.

As used herein, the term "pharmaceutically acceptable derivative", means any pharmaceutically acceptable salt, solvate, N-oxide and/or prodrug (e.g. esters, carbamates, phosphate esters) of a compound of the invention, which upon administration to the recipient is capable of providing (directly or indirectly) a compound of formula (I) of the invention, or an active metabolite or residue thereof. For example, pharmaceutically acceptable derivatives includes compounds of formula (I) that have been covalently modified with a group that undergoes at least some in vivo cleavage to a compound of formula (I). The invention extends to all such derivatives. Such derivatives are recognizable to those skilled in the art, without undue experimentation. Nevertheless, reference is made to the teaching of Burger's Medicinal Chemistry and Drug Discovery, 5th Edition, Vol 1: Principles and Practice, which is incorporated herein by reference to the extent of teaching such derivatives.

Prodrugs are compounds derived from a compound of a formula (I) and a promoiety which is covalently bonded to the compound of formula (I). The compound of formula (I) is released in vivo, after administration of the prodrug to a patient. Prodrugs are generally prepared by modifying functional groups in a way such that the modification is cleaved, either by routine manipulation or in vivo, yielding the parent compound. Prodrugs include, for example, compounds of formula (I) of this invention wherein hydroxy, amine or sulfhydryl groups are bonded to any group that, when administered to a patient, cleaves to form the hydroxy, amine or sulfhydryl groups. Representative examples of prodrugs include (but are not limited to) acetate, formate and benzoate derivatives of alcohol, sulfhydryl and amine functional groups of the compounds of structure (I). Further, in the case of a carboxylic acid (—COOH), esters may be employed, such as methyl esters, ethyl esters, and the like. Esters may be active in their own right and/or be hydrolysable under in vivo conditions in the human body. Suitable pharmaceutically acceptable in vivo hydrolysable ester groups include those which break down readily in the human body to leave the parent acid or its salt.

Prodrugs are converted within the body, e.g. by hydrolysis in the blood, into its active form that has medical effects. Pharmaceutically acceptable prodrugs include those described in T. Higuchi and V. Stella, Prodrugs as Novel Delivery Systems, Vol. 14 of the A.C.S. Symposium Series, Edward B. Roche, ed., Bioreversible Carriers in Drug Design, American Pharmaceutical Association and Pergamon Press, 1987, and in D. Fleisher, S. Ramon and H. Barbra "Improved oral drug delivery: solubility limitations overcome by the use of prodrugs", Advanced Drug Delivery Reviews (1996) 19 (2) 115-130, each of which are incorporated herein by reference.

Those skilled in the art of organic chemistry will appreciate that many organic compounds can form complexes with solvents in which they are reacted or from which they are precipitated or crystallized. These complexes are known as solvates. For example, a complex with water is known as a "hydrate". Some of the compounds of this invention may be crystallised or recrystallised from solvents such as aqueous and organic solvents. In such cases solvates may be formed. Solvates of the compounds of the invention are within the scope of the invention. For example, this invention includes within its scope stoichiometric solvates including hydrates as well as compounds containing variable amounts of water or other solvent that may be produced by processes such as lyophilisation.

The present invention includes any pharmaceutically acceptable combination of derivatives of compounds of formula (I). Thus non-limiting examples, used here for illustrative purposes, may include a pharmaceutically acceptable salt of a compound of formula (I) that is further present as a solvate, or a pharmaceutically acceptable prodrug of a salt and/or solvate of a compound of formula (I).

Since the compounds of formula (I) are intended for use in pharmaceutical compositions it will readily be understood that they are each provided in substantially pure form, for example at least 60% pure, more suitably at least 75% pure and preferably at least 85%, especially at least 98% pure (% are on a weight for weight basis). Impure preparations of the compounds may be used for preparing the more pure forms used in the pharmaceutical compositions; these less pure preparations of the compounds should contain at least 1%, more suitably at least 5%, e.g., from 10 to 59% of a compound of the formula (I) or pharmaceutically acceptable derivative thereof.

Pharmaceutically acceptable salts of the above-mentioned compounds of formula (I) include the free base form or their acid addition or quaternary ammonium salts, for example their salts with mineral acids e.g. hydrochloric, hydrobromic, sulphuric, nitric or phosphoric acids, or organic acids, e.g. acetic, fumaric, succinic, maleic, citric, benzoic, p-toluenesulphonic, methanesulphonic, naphthalenesulphonic or tartaric acids. One of skill in the art will recognize that where compounds of the invention contain multiple basic sites, a compound of the invention may be present as a salt complexed with more than one equivalents of a corresponding acid or mixture of acids.

Compounds of formula (I) having a free carboxy group may also be prepared as an in vivo hydrolysable ester.

Examples of suitable pharmaceutically acceptable in vivo hydrolysable ester-forming groups include those forming esters which break down readily in the human body to leave the parent acid or its salt.

Suitable groups of this type include those of part formulae (i), (ii), (iii), (iv) and (v):

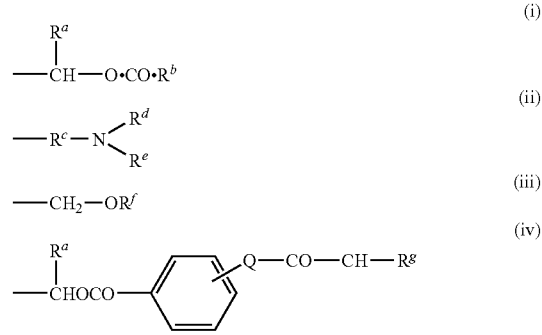

-continued

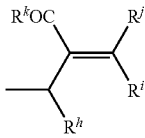
(v)

wherein $R^a$ is hydrogen, $(C_{1-6})$ alkyl, $(C_{3-7})$ cycloalkyl, methyl, or phenyl, $R^b$ is $(C_{1-6})$ alkyl, $(C_{1-6})$alkoxy, phenyl, benzyl, $(C_{3-7})$cycloalkyl, $(C_{3-7})$cycloalkyloxy, $(C_{1-6})$alkyl $(C_{3-7})$ cycloalkyl, 1-amino$(C_{1-6})$alkyl, or 1-$(C_{1-6}$ alkyl)amino$(C_{1-6})$ alkyl; or $R^a$ and $R^b$ together form a 1,2-phenylene group optionally substituted by one or two methoxy groups; $R^c$ represents $(C_{1-6})$alkylene optionally substituted with a methyl or ethyl group and $R^d$ and $R^e$ independently represent $(C_{1-6})$ alkyl; $R^f$ represents $(C_{1-6})$ alkyl; $R^g$ represents hydrogen or phenyl optionally substituted by up to three groups selected from halogen, $(C_{1-6})$ alkyl, or $(C_{1-6})$ alkoxy; Q is oxygen or NH; $R^h$ is hydrogen or $(C_{1-6})$ alkyl; $R^i$ is hydrogen, $(C_{1-6})$ alkyl optionally substituted by halogen, $(C_{2-6})$ alkenyl, $(C_{1-6})$alkoxycarbonyl, aryl or heteroaryl; or $R^h$ and $R^i$ together form $(C_{1-6})$ alkylene; $R^j$ represents hydrogen, $(C_{1-6})$ alkyl or $(C_{1-6})$alkoxycarbonyl; and $R^k$ represents $(C_{1-8})$alkyl, $(C_{1-8})$alkoxy, $(C_{1-6})$alkoxy $(C_{1-6})$alkoxy or aryl.

Examples of suitable in vivo hydrolysable ester groups include, for example, acyloxy$(C_{1-6})$alkyl groups such as acetoxymethyl, pivaloyloxymethyl, acetoxyethyl, pivaloyloxyethyl, 1-(cyclohexylcarbonyloxy)prop-1-yl, and (1-aminoethyl)carbonyloxymethyl; $(C_{1-6})$alkoxycarbonyloxy$(C_{1-6})$ alkyl groups, such as ethoxycarbonyloxymethyl, ethoxycarbonyloxyethyl and propoxycarbonyloxyethyl; di$(C_{1-6})$alkylamino$(C_{1-6})$alkyl especially di$(C_{1-4})$alkylamino $(C_{1-4})$alkyl groups such as dimethylaminomethyl, dimethylaminoethyl, diethylaminomethyl or diethylaminoethyl; 2-$(C_{1-6})$alkoxycarbonyl)-2-$(C_{2-6})$alkenyl groups such as 2-(isobutoxycarbonyl)pent-2-enyl and 2-(ethoxycarbonyl) but-2-enyl; lactone groups such as phthalidyl and dimethoxyphthalidyl.

A further suitable pharmaceutically acceptable in vivo hydrolysable ester-forming group is that of the formula:

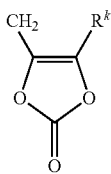

wherein $R^k$ is hydrogen, $C_{1-6}$ alkyl or phenyl.

R is preferably hydrogen.

Compounds of formula (I) may also be prepared as the corresponding N-oxides.

The compounds of formula (I) may have one or more asymmetric carbon atoms giving rise to optical- or stereoisomers, and may occur as racemates, mixtures of isomers in all ratios, e.g., racemic mixtures, and as individual enantiomers or diastereomers. The invention includes all such isomeric forms, including pure isomeric forms.

Where a compound of the invention contains an alkenyl or alkenylene group, cis (E) and trans (Z) isomerism may also occur. The present invention includes the individual stereoisomers of the compounds of the invention and, where appropriate, the individual tautomeric forms thereof, together with mixtures thereof.

The different isomeric forms may be separated or resolved one from the other by conventional methods, or any given isomer may be obtained by conventional synthetic methods or by stereospecific or asymmetric syntheses.

Furthermore, those skilled in the art of organic chemistry will appreciate that organic compounds in crystalline form may exist as polymorphs. Polymorphs of compounds or derivatives of the invention are within the scope of the invention.

In a further aspect of the invention there is provided a process for preparing compounds of formula (I), and derivatives thereof.

Compounds of formula (I) wherein $W_1$ is $CR_5$ may be formed by a process comprising one or more of the following steps.

A suitable phenol (having the desired $R_1$, $R_2$ groups) (e.g., halophenol such as bromophenol, or o-triflate) is reacted with a suitable formylation reagent such as paraformaldehyde to form a salicylaldehyde. Suitable reagents and methodology are known in the art, or reagents can be prepared analogously to reagents known in the art using standard chemistry techniques.

The salicylaldehyde is then converted to a chromenone derivative. For example, the aldehyde group of the salicylaldehyde is converted to an acrylate (e.g., ethyl acrylate), which is then cyclized (reaction of the alcohol and acrylate groups) to form the chromenone. This may be accomplished using standard chemistry techniques.

The substituted (e.g., halogenated) chromenone derivative is reacted with a suitable acetylene (providing desired A-$CH_2$, $R_6$ and $R_7$ groups) to form an acetylene derivative having a protected amine group. Suitably this reaction is conducted using a palladium catalyst and in a suitable solvent, typically in the presence of an acid scavenger (e.g., base). Suitable acetylene reagents are 4-amino-1-ethynylcyclohexanes wherein the amino group is protected. Such acetylene reagents may be prepared from known reagents by methods known in the art.

The acetylene derivative is reduced to form a saturated derivative, for example via a hydrogenation reaction using palladium catalyst and in a suitable solvent.

The protecting group is removed from the saturated derivative to form an amine, suitably by subjecting the derivative to standard acidic conditions.

The amine is then converted to a compound of formula I, for example via reductive amination. For example, the amine may be reacted with a suitable aldehyde (having the desired $R_8$ group) in a suitable solvent to provide the intermediate imine, which is then reacted with a suitable reducing agent to provide the compound of formula I. Suitable aldehyde reagents containing the required $R_8$ group are known compounds or may be prepared analogously to known compounds, see for example WO02/08224, WO02/50061, WO02/56882, WO02/96907, WO2003087098, WO2003010138, WO2003064421, WO2003064431, WO2004002992, WO2004002490, WO2004014361, WO2004041210, WO2004096982, WO2002050036, WO2004058144, WO2004087145, WO06002047, WO06014580, WO06010040, WO06017326, WO06012396, WO06017468, WO06020561 and EP0559285.

Compounds of formula (I) wherein $W_1$ is N may be formed by a process comprising one or more of the following steps.

A suitably substituted salicylaldehyde, such as commercially available 2-hydroxy-3-(2-propen-1-yl)benzaldehyde, is converted to a chromenone derivative. This may be accomplished using standard chemistry techniques. For example, the salicylaldehyde is heated in a mixture of triethylamine and acetic anhydride under thermal or microwave conditions to form the chromenone.

The propenyl group is then converted to an acetaldehyde derivative. For example, treatment of an 8-(2-propen-1-yl)-2H-chromen-2-one with a mixture of osmium tetroxide and sodium periodate using standard chemistry techniques results in the formation of the desired acetaldehyde derivative. Alternate techniques such as treatment of the 8-(2-propen-1-yl)-2H-chromen-2-one under ozonolysis conditions may also be used.

The chromenone acetaldehyde is reacted with a suitable amine (providing desired $CH_2$, $R_6$ and $R_7$ groups) such as 4-amino-1-piperidines wherein the 4-amino group is protected. The amine may be reacted with a suitable aldehyde in a suitable solvent to provide the intermediate imine, which is then reacted with a suitable reducing agent to provide the desired compound. Such amine reagents may be prepared from known reagents by methods known in the art.

The protecting group is removed from the above derivative to form an amine, suitably by subjecting the derivative to standard acidic conditions. The amine is converted to a compound of formula I, for example in the manner described above for preparing compounds wherein $W_1$ is $CR_5$.

Chemistry techniques applicable to preparation of compounds of the invention are described in the literature, for example, WO99/37635, WO00/21948, WO00/43383, WO00/78748, WO01/07432, WO 02/08224, WO 02/24684, WO02/50061, WO02/50040, WO 02/056882, WO 02/096907, WO 03/087098, WO03/010138, WO03/064431, WO03/064421, WO04/002992, WO04/002490, WO04/014361, WO04/058144, WO06/002047, WO06/014580, and WO06/020561.

Further details for the preparation of compounds of formula (I) are found in Schemes 1 and 2, and in the examples set forth herein.

One of skill in the readily appreciates that optimization for a given reaction may require some routine variation in reaction parameters such as reaction time, temperature, energy source, pressure, light, pressure, solvent or solvents used, co-reagents, catalysts, and the like.

The antibacterial compounds according to the invention may be formulated for administration in any convenient way for use in human or veterinary medicine, by analogy with other antibacterials.

The pharmaceutical compositions of the invention include those in a form adapted for oral, topical or parenteral use and may be used for the treatment of bacterial infection in mammals including humans.

The composition may be formulated for administration by any route. The compositions may be in the form of tablets, capsules, powders, granules, lozenges, creams or liquid preparations, such as oral or sterile parenteral solutions or suspensions.

The topical formulations of the present invention may be presented as, for instance, ointments, creams or lotions, eye ointments and eye or ear drops, impregnated dressings and aerosols, and may contain appropriate conventional additives such as preservatives, solvents to assist drug penetration and emollients in ointments and creams.

The formulations may also contain compatible conventional carriers, such as cream or ointment bases and ethanol or oleyl alcohol for lotions. Such carriers may be present as from about 1% up to about 98% of the formulation. More usually they will form up to about 80% of the formulation.

Tablets and capsules for oral administration may be in unit dose presentation form, and may contain conventional excipients such as binding agents, for example syrup, acacia, gelatin, sorbitol, tragacanth, or polyvinylpyrrolidone; fillers, for example lactose, sugar, maize-starch, calcium phosphate, sorbitol or glycine; tabletting lubricants, for example magnesium stearate, talc, polyethylene glycol or silica; disintegrants, for example potato starch; or acceptable wetting agents such as sodium lauryl sulphate. The tablets may be coated according to methods well known in normal pharmaceutical practice. Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives, such as suspending agents, for example sorbitol, methyl cellulose, glucose syrup, gelatin, hydroxyethyl cellulose, carboxymethyl cellulose, aluminium stearate gel or hydrogenated edible fats, emulsifying agents, for example lecithin, sorbitan monooleate, or acacia; non-aqueous vehicles (which may include edible oils), for example almond oil, oily esters such as glycerine, propylene glycol, or ethyl alcohol; preservatives, for example methyl or propyl p-hydroxybenzoate or sorbic acid, and, if desired, conventional flavouring or colouring agents.

Suppositories will contain conventional suppository bases, e.g. cocoa-butter or other glyceride.

For parenteral administration, fluid unit dosage forms are prepared utilizing the compound and a sterile vehicle, water being preferred. The compound, depending on the vehicle and concentration used, can be either suspended or dissolved in the vehicle. In preparing solutions the compound can be dissolved in water for injection and filter sterilised before filling into a suitable vial or ampoule and sealing.

Advantageously, agents such as a local anaesthetic, preservative and buffering agents can be dissolved in the vehicle. To enhance the stability, the composition can be frozen after filling into the vial and the water removed under vacuum. The dry lyophilized powder is then sealed in the vial and an accompanying vial of water for injection may be supplied to reconstitute the liquid prior to use. Parenteral suspensions are prepared in substantially the same manner except that the compound is suspended in the vehicle instead of being dissolved and sterilization cannot be accomplished by filtration. The compound can be sterilised by exposure to ethylene oxide before suspending in the sterile vehicle. Advantageously, a surfactant or wetting agent is included in the composition to facilitate uniform distribution of the compound.

The compositions may contain from 0.1% by weight, preferably from 10-60% by weight, of the active material, depending on the method of administration. Where the compositions comprise dosage units, each unit will preferably contain from 50-500 mg of the active ingredient. The dosage as employed for adult human treatment will preferably range from 100 to 3000 mg per day, for instance 1500 mg per day depending on the route and frequency of administration. Such a dosage corresponds to 1.5 to 50 mg/kg body weight per day. Suitably the dosage is from 5 to 30 (e.g., 5 to 20) mg/kg body weight per day.

The compound of formula (I) may be the sole therapeutic agent in the compositions of the invention or a combination with other antibacterials. If the other antibacterial is a β-lactam then a β-lactamase inhibitor may also be employed.

Compounds of formula (I) are active against a wide range of organisms including both Gram-negative and Gram-positive organisms. Some compounds of formula (I) may be active against more than one organism. This may be readily determined by test methods described herein.

No unacceptable toxicological effects are expected when a compound of this invention is administered in the above mentioned dosage range.

It is to be understood that the present invention covers all combinations of particular and preferred groups described herein above.

All publications, including but not limited to patents and patent applications, cited in this specification are herein incorporated by reference (whether specifically stated to be so or not) as if each individual publication were specifically and individually indicated to be incorporated by reference herein as though fully set forth.

The following examples illustrate the preparation of certain compounds of formula (I) and the activity of certain compounds of formula (I) against various bacterial organisms.

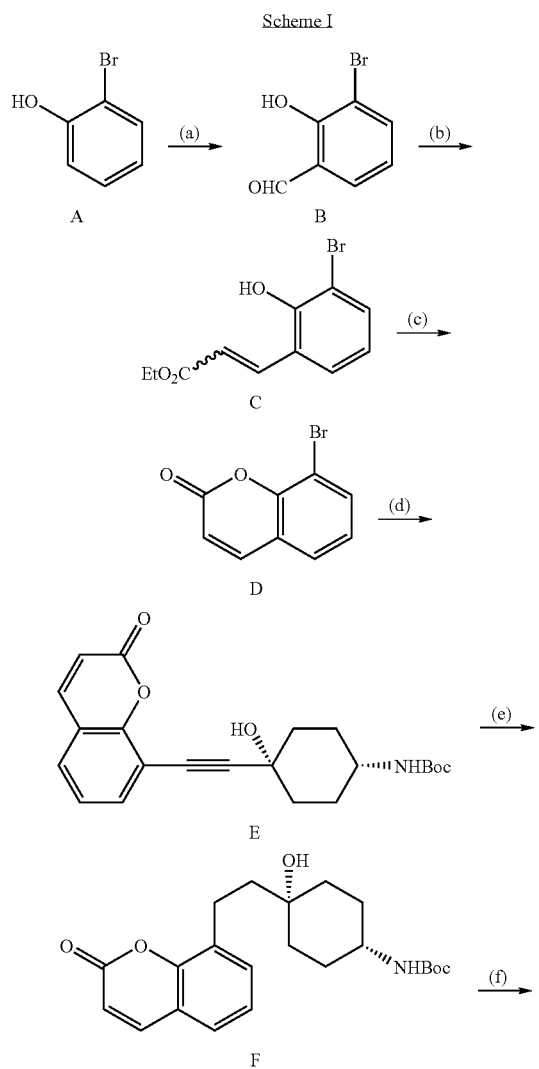

Scheme I

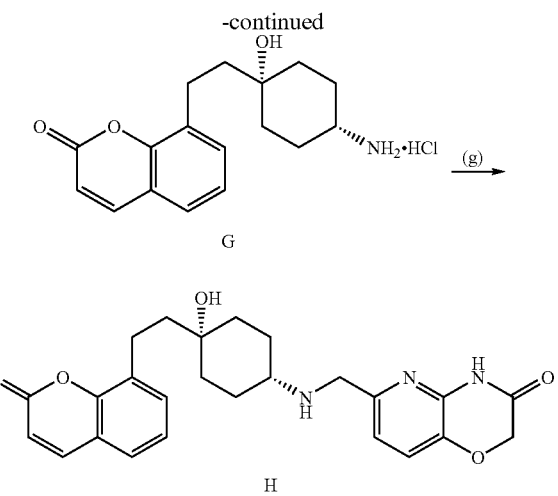

(a) $(CH_2O)_n$, $MgCl_2$, $Et_3N$, $CH_3CN$, reflux; (b) $Ph_3P$═$CHCO_2Et$, solvent; (c) N-methylpyrrolidinone, 190-200° C.; (d) cis-4-(tert-butoxycarbonylamino)-1-ethynylcyclohexanol, $(Ph_3P)_2PdCl_2$, $Et_3N$, DMF; (e) $H_2$, Pd/C, EtOH; (f) 4 M HCl/dioxane, MeOH, $CH_2Cl_2$; (g) $NaHCO_3$, 3-oxo-3,4-dihydro-2H-pyrido[3,2-b][1,4]oxazine-6-carbaldehyde, $Na_2SO_4$, $NaBH(OAc)_3$, MeOH, $CH_2Cl_2$.

Commercially available 2-bromophenol A is formulated according to the procedure of Verner and coworkers (*J. Med. Chem.* 2001, 44, 2753-2771) to afford the known 3-bromosalicylaldehyde B. Many other methods for the formation of salicylaldehydes from phenols are known to those skilled in the art, and may be used to prepare a variety of derivatives. The salicylaldehyde B can be converted to the chromanone derivative D by standard, well-documented chemistry. For example, reaction of aldehyde B with (carbethoxymethylene)triphenylphosphorane affords acrylate C, which can be cyclized conveniently to the known chromanone D (*Chem. Pharm. Bull.* 1994, 42, 2170-2173; *Heterocycles* 2003, 59, 217-224) on heating in an appropriate solvent, such as N-methylpyrrolidinone. Compound D reacts with acetylenes, for instance cis-4-(tert-butoxycarbonylamino)-1-ethynylcyclohexanol, under palladium catalysis, to afford derivative E. Typically, the preferred palladium catalyst is bis(triphenylphosphine)palladium (II) chloride, and dimethylformamide (DMF) is generally the solvent of choice. An appropriate base, for example triethylamine or diisopropylethylamine, is normally included as an acid scavenger. Reduction of the acetylenic group of E is conveniently accomplished by hydrogenation in the presence of a palladium catalyst, generally palladium on activated charcoal, in a suitable solvent, such as MeOH, EtOH, i-PrOH, EtOAc, or mixtures thereof, to afford the saturated derivative F. The tert-butyl carbamate (Boc) protecting group of F is removed under standard acidic conditions (see Greene "Protective Groups in Organic Synthesis" (published by Wiley-Interscience), to afford amine G, which is converted to H through a reductive amination procedure. This method, which is well-known to those of skill in the art, involves the initial conversion of an aldehyde to an intermediate imine, which is subsequently reduced, oftentimes in situ, to afford the amine. For example, the amine G reacts with a suitable aldehyde, such as 3-oxo-3,4-dihydro-2H-pyrido[3,2-b][1,4]oxazine-6-carbaldehyde, in a suitable solvent, typically DMF, $CH_3CN$, MeOH, $CH_2Cl_2$, or mixtures thereof, to afford an intermediate imine (not shown). Reaction of this intermediate imine with a suitable reducing agent, for example sodium borohydride, sodium cyanoborohydride or sodium (triacetoxy)borohydride, gives the compound H.

Scheme 2

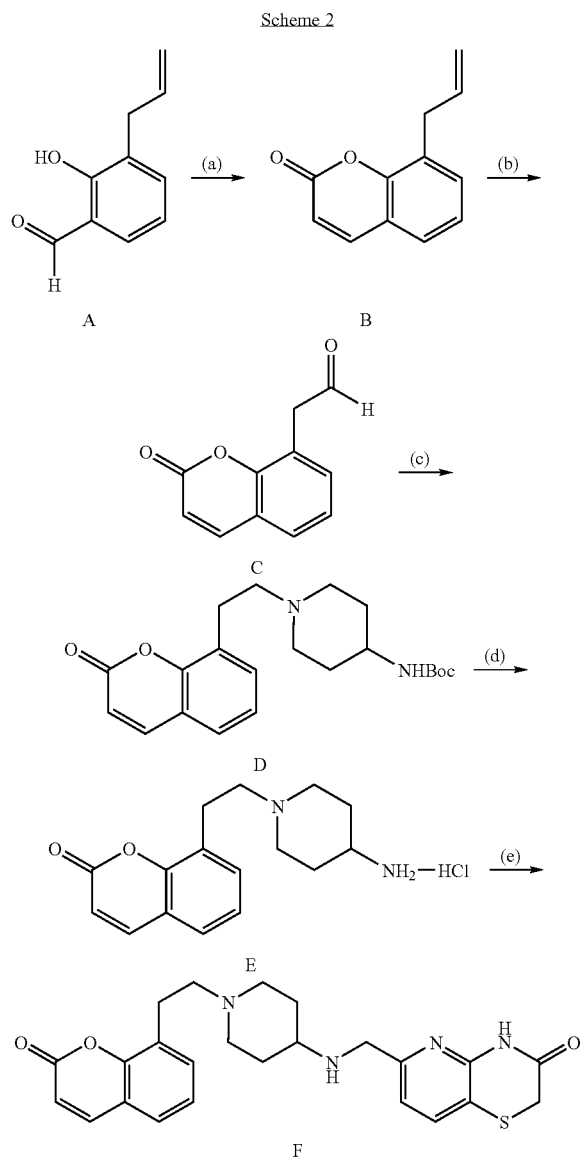

(a) Ac₂O, Et₃N, Microwave heating: 160° C., 45 min. (b) OsO₄, NaIO₄, dioxane, H₂O
(c) 4-N-Boc aminopiperidine, MeOH, CH₂Cl₂, NaBH(OAc)₃, (d) 4 M HCl/dioxane,
MeOH, CH₂Cl₂; (e) Et₃N, 3-oxo-3,4-dihydro-2H-pyrido[3,2-b][1,4]thiazine-6-
carboxaldehyde, NaBH₄, MeOH, CH₂Cl₂.

Commercially available 3-allylsalicylaldehyde A is heated in a mixture of acetic anhydride and triethyl amine to afford the desired chromenone derivative B. Many other methods for the formation of chromenones derived from salicylaldehydes are known to those skilled in the art, and may be used to prepare a variety of derivatives. The 8-(2-propen-1-yl) (i.e. allyl) group can be converted to an acetaldehyde derivative C via treatment with osmium tetroxide and sodium periodate in a suitable solvent system such as 2:1 1,4-dioxane:H₂O. Alternative oxidative cleavage methods such as ozonolysis are known to those skilled in the art, and may be used to prepare like derivatives. Chromenone acetaldehyde derivative C reacts with amines, for instance 4-(tert-butoxycarbonylamino)-1-piperidine, in a suitable solvent such as DMF, CH₃CN, MeOH, CH₂Cl₂, or mixtures thereof, to afford an intermediate imine (not shown). Reaction of this intermediate imine with a suitable reducing agent, for example sodium borohydride, sodium cyanoborohydride or sodium (triacetoxy)borohydride, gives the compound D. The tert-butyl carbamate (Boc) protecting group of D is removed under standard acidic conditions (see Greene "Protective Groups in Organic Synthesis" (published by Wiley-Interscience), to afford amine E, which is converted to F through a reductive amination procedure. This method, which is well-known to those of skill in the art, involves the initial conversion of an aldehyde to an intermediate imine, which is subsequently reduced, oftentimes in situ, to afford the amine. For example, the amine E reacts with a suitable aldehyde, such as 2H-pyrido[3,2-b][1,4]thiazin-3(4H)-one 6-carbaldehyde, in a suitable solvent, typically DMF, CH₃CN, MeOH, CH₂Cl₂, or mixtures thereof, to afford an intermediate imine (not shown). Reaction of this intermediate imine with a suitable reducing agent, for example sodium borohydride, sodium cyanoborohydride or sodium (triacetoxy)borohydride, gives the compound F.

General

Proton nuclear magnetic resonance (¹H NMR) spectra were recorded at either 300 or 400 MHz, and chemical shifts are reported in parts per million (δ) downfield from the internal standard tetramethylsilane (TMS). Abbreviations for NMR data are as follows: s=singlet, d=doublet, t=triplet, q=quartet, m=multiplet, dd=doublet of doublets, dt=doublet of triplets, app=apparent, br=broad. J indicates the NMR coupling constant measured in Hertz. CDCl₃ is deuteriochloroform, DMSO-d₆ is hexadeuteriodimethylsulfoxide, and CD₃OD is tetradeuteriomethanol. Mass spectra were obtained using electrospray (ES) ionization techniques. Elemental analyses were performed by Quantitative Technologies Inc., Whitehouse, N.J. Melting points were obtained on a Thomas-Hoover melting point apparatus and are uncorrected. All temperatures are reported in degrees Celsius. Analtech Silica Gel GF and E. Merck Silica Gel 60 F-254 thin layer plates were used for thin layer chromatography. Flash chromatography was carried out on E. Merck Kieselgel 60 (230-400 mesh) silica gel. Preparative HPLC was performed using ISCO chromatography systems. Celite® is a filter aid composed of acid-washed diatomaceous silica, and is a registered trademark of Manville Corp., Denver, Colo.

Preparation 1

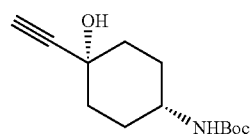

Preparation of cis-4-(tert-butoxycarbonyl)amino-1-ethynylcyclohexanol a) cis-4-(tert-Butoxycarbonyl)amino-1-[(triisopropylsilyl)ethynyl]cyclohexanol A solution of triisopropylsilyl acetylene (18.24 g, 0.10 mol) in THF (50 mL) at −78° C. was treated with n-butyllithium (1.6 M solution in hexanes; 62.5 mL, 0.10 mol). The reaction mixture was stirred at −78° C. for 30 min, then was added dropwise over a period of 30 min to a solution of N-4-Boc-aminocyclohexanone (10.6 g, 0.050 mol; Astatech,

(b) 8-Bromo-6-chloro-2H-chromen-2-one

A solution of methyl (2E)-3-(3-bromo-5-chloro-2-hydroxyphenyl)-2-propenoate (1.45 g; 5.0 mmol) in decalin (5 mL) was heated in a sand bath at 200° C. for 48 h. The reaction was then cooled to RT and hexanes (10 mL) was added. The solid was collected by suction filtration and washed with hexanes. Drying under high vacuum gave the title compound (1.2 g, 95%) as a tan solid: $^1$H NMR (400 MHz, DMSO-d$_6$) δ 7.78 (s, 1H), 7.63 (d, J=9.6 Hz, 1H)), 7.46 (s, 1H), 6.52 (d, J=9.6 Hz, 1H); MS (ES) m/e 259, 261 (M+H)$^+$.

(c) 8-[(cis-4-(tert-Butoxycarbonyl)amino-1-hydroxycyclohexyl)ethynyl]-6-chloro-2H-chromen-2-one A solution of 8-bromo-6-chloro-2H-chromen-2-one (520 mg, 2.0 mmol), cis-4-(tert-butoxycarbonyl)amino-1-ethynylcyclohexanol (480 mg, 2.0 mmol), Pd(Ph$_3$P)$_2$Cl$_2$ (140 mg, 0.20 mmol), and CuI (20 mg, 0.10 mmol) in DMF (2 mL) and Et$_3$N (1 mL) was placed in a 5 mL microwave reactor vessel. The reaction was irradiated at 120° C. for 10 min, then was cooled to RT and concentrated under reduced pressure. Flash chromatography on silica gel (5% MeOH/CHCl$_3$) gave the title compound (485 mg, 58%) as a colorless oil: MS (ES) m/e 418, 420 (M+H)$^+$.

(d) 8-[2-(cis-4-(tert-Butoxycarbonyl)amino-1-hydroxycyclohexyl)ethyl]-6-chloro-2H-chromen-2-one To a solution of 8-[(cis-4-(tert-butoxycarbonyl)amino-1-hydroxycyclohexyl)ethynyl]-6-chloro-2H-chromen-2-one (250 mg, 0.60 mmol) in ethanol (10 mL) was added 10% palladium on carbon (20 mg). The mixture was hydrogenated (25 psi) on a Parr apparatus for 3 h, then the hydrogen was removed and the resulting mixture was filtered through a pad of Celite®. The filtrate was concentrated under reduced pressure and the residue was purified by flash chromatography on silica gel (5% MeOH/CHCl$_3$) to afford the title compound (150 mg, 60%) as a colorless oil: MS (ES) m/e 422, 424 (M+H)$^+$.

(e) 8-[2-(cis-4-amino-1-hydroxycyclohexyl)ethyl]-6-chloro-2H-chromen-2-one, hydrochloride To a solution of 8-[2-(cis-4-(tert-butoxycarbonyl)amino-1-hydroxycyclohexyl)ethyl]-6-chloro-2H-chromen-2-one (150 mg, 0.35 mmol) in CH$_2$Cl$_2$ (2 mL) at RT was added a solution of HCl in dioxane (4 M, 0.2 mL, 0.80 mmol). The reaction was allowed to stir for 14 h then was concentrated under reduced pressure to afford the title compound (110 mg, 88%) as a yellow solid: MS (ES) m/e 322, 324 (M+H)$^+$.

Inc) in diethyl ether (1000 mL) at −78° C. The resulting mixture was stirred at −78° C. for 1 hr, then was allowed to slowly warm to RT over 4 hr. The reaction was quenched with saturated NH$_4$Cl, diluted with EtOAc (500 mL), and washed sequentially with saturated aqueous NaHCO$_3$ solution (100 mL), H$_2$O (100 mL), and saturated aqueous NaCl solution (100 mL). The organic layer was dried (MgSO$_4$) and concentrated to yield the title compound as an off-white foam: MS (ES) m/e 396 (M+H)$^+$. This material was used without further purification.

b) cis-4-(tert-Butoxycarbonyl)amino-1-ethynylcyclohexanol

A solution of crude cis-4-(tert-butoxycarbonyl)amino-1-[(triisopropylsilyl)ethynyl]cyclohexanol (19.8 g, 0.10 mol) in THF (100 mL) at 0° C. was treated with TBAF (1 N solution in THF; 150 mL, 0.15 mol) and allowed to warm to RT with stirring. After 8 hr, the solvent was removed in vacuo and the residue was partitioned between EtOAc (500 mL) and aqueous NaCl (100 mL). The layers were separated and the organic layer was dried over MgSO$_4$ and concentrated under reduced pressure. The residue was purified by chromatography on silica gel (gradient: 20-25% EtOAc/hexanes) to yield the title compound (6.4 g, 53%) as a white solid: TLC (25% EtOAc/hexanes) R$_f$ 0.25; MS (ES) m/e 240 (M+H)$^+$. The isomeric 1,1-dimethylethyl(trans-4-hydroxy-4-{[tris(1-methylethyl)silyl]ethynyl}cyclohexyl)carbamate (2.0 g, 17%) was isolated as an tan foam: TLC (25% EtOAc/hexanes) R$_f$ 0.15; MS (ES) m/e 240 (M+H)$^+$.

Preparation 2

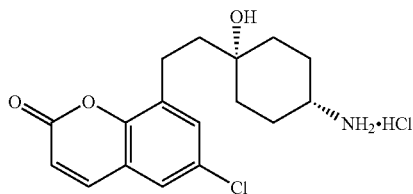

Preparation of 8-[2-(cis-4-amino-1-hydroxycyclohexyl)ethyl]-6-chloro-2H-chromen-2-one hydrochloride

(a) Methyl (2E)-3-(3-bromo-5-chloro-2-hydroxyphenyl)-2-propenoate

To a solution of bis(2,2,2-trifluoroethyl)(methoxycarbonylmethyl)phosphonate (3.18 g, 10.0 mmol) in THF (100 mL) at −78° C. was added 18-crown-6 (13.2 g, 50.0 mmol). The solution was stirred for 10 min then a solution of potassium hexamethyldisilazide in THF (0.91 M, 11.0 mL, 10.0 mmol) was added slowly. The reaction was stirred for 20 min then 3-bromo-5-chloro-2-hydroxy benzaldehyde (2.35 g, 10 mmol) was added. The reaction was allowed to stir at −78° C. for 2 hr, then was quenched with saturated NH$_4$Cl (20 mL) The mixture was extracted with Et$_2$O (3×100 mL) and the organic layer was dried (Na$_2$SO$_4$) and concentrated. Flash chromatography on silica gel (15% EtOAc/hexanes) gave, the title compound (2.48 g, 85%) as a yellow solid: $^1$H NMR (400 MHz, DMSO-d$_6$) δ 7.88 (d, J=16.0 Hz, 1H), 7.50 (s, 1H), 7.44 (s, 1H), 6.57 (d, J=16.0 Hz, 1H), 3.84 (s, 3H); MS (ES) m/e 291, 293 (M+H)$^+$.

Preparation 3

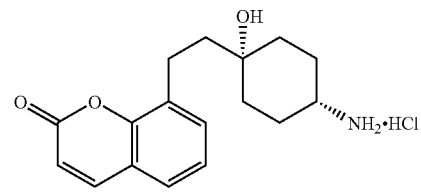

Preparation of 8-[2-(cis-4-amino-1-hydroxycyclo-hexyl)ethyl]-2H-chromen-2-one, hydrochloride

(a) 3-Bromo-2-hydroxybenzaldehyde

To a solution of 2-bromophenol (3.17 g, 18.3 mmol) in acetonitrile (85 mL) was added magnesium chloride (2.62 g, 27.5 mmol), paraformaldehyde (3.7 g, 0.13 mmol) and Et$_3$N (6.4 ml, 46 mmol). The reaction was heated at reflux for 3 h, allowed to cool, diluted with 1 N HCl (100 mL, and extracted with ethyl acetate. The organic layer was washed with aqueous sodium chloride, dried (MgSO$_4$), and concentrated to afford the title compound (3.74 g, 100%): MS (ES) m/e 202.1 (M+H)$^+$. This was used without further purification.

(b) 8-Bromo-2H-chromen-2-one

To a solution of 3-bromo-2-hydroxybenzaldehyde (402 mg, 2.0 mmol) in NMP (5 mL) was added carbethoxymethylene triphenylphosphorane (765 mg, 2.2 mmol). The reaction was heated at 210° C. for 3 h, then was cooled to RT and partitioned between water and ethyl acetate. The layers were separated and the organic layer was dried over MgSO$_4$. Purification by flash chromatography on silica gel (2:1 hexanes/ethyl acetate) yielded the title compound (116 mg, 26%) as a light beige solid: MS (ES) m/e 227.0 (M+H)$^+$.

(c) 8-[(cis-4-(tert-Butoxycarbonyl)amino-1-hydroxy-cyclohexyl)ethynyl]-2H-chromen-2-one To a solution of 8-bromo-2H-chromen-2-one (115.8 mg, 0.51 mmol) in 6:4 DMF/Et$_3$N (1.2 mL) in a 5 mL Emrys process vial was added cis-4-(tert-butoxycarbonyl)amino-1-ethynylcyclohexanol (122 mg, 0.51 mmol), CuI (4.8 mg, 0.025 mmol) and dichlorobis(triphenylphosphine) palladium (II) (36 mg, 0.087 mmol). The reaction was heated at 120° C. for 10 min in an Emrys Optimizer Microwave reactor then was cooled to RT and partitioned between water and ethyl acetate. The layers were separated and the organic layer was dried over MgSO$_4$. Purification by flash chromatography on silica gel (gradient elution: 1% to 5% MeOH/CH$_2$Cl$_2$) yielded the title compound (139 mg, 70%) as an off-white solid: MS (ES) m/e 392.0 (M+H)$^+$.

(d) 8-[2-(cis-4-(tert-Butoxycarbonyl)amino-1-hydroxycyclohexyl)ethyl]-2H-chromen-2-one To a solution of 8-[(cis-4-(tert-butoxycarbonyl)amino-1-hydroxycyclohexyl)ethynyl]-2H-chromen-2-one (139 mg, 0.36 mmol) in EtOH (10 mL) was added 10% palladium on carbon (40 mg, 50% by weight with water). The mixture was hydrogenated at 25 psi for 2 h, filtered through a pad of Celite®, and concentrated to give the title compound (133 mg, 97%) as a pale yellow oil: MS (ES) m/e 388.4 (M+H)$^+$.

(e) 8-[2-(cis-4-Amino-1-hydroxycyclohexyl)ethyl]-2H-chromen-2-one, hydrochloride To a solution of 8-[2-(cis-4-(tert-butoxycarbonyl)amino-1-hydroxycyclohexyl)ethyl]-2H-chromen-2-one (133 mg, 0.34 mmol) in 1:9 MeOH/CH$_2$Cl$_2$ (3 mL) at 0° C. was added a solution of HCl in dioxane (4 M, 0.25 mL). The reaction was warmed to RT and stirred for 16 h, then the solvents were removed under reduced pressure to afford the title compound (123 mg, 100%) as a pale yellow solid: MS (ES) m/e 288.2 (M+H)$^+$.

Preparation 4

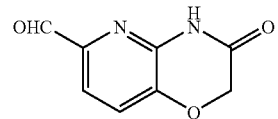

Preparation of 3-oxo-3,4-dihydro-2H-pyrido[3,2-b][1,4]oxazine-6-carboxaldehyde

(a) 2-Bromo-5-hydroxy-6-nitropyridine

3-Hydroxy-2-nitropyridine (100 g, 0.714 mole) was dissolved in DMF (1 L), the solution was cooled to 0° C., and N-bromosuccinimide (165 g, 0.927 mole) was added portionwise over 5 hr. The mixture was then stirred at RT for 15 hr and concentrated in vacuo. The residue was taken up in Et$_2$O (500 mL) and the mixture was stirred for 30 min. The precipitate was removed by suction filtration, and the filtrate was concentrated in vacuo to afford the title compound (180 g): MS (ES) m/e 219.0 (M+H)$^+$. This material was used without further purification.

(b) Ethyl (6-bromo-2-nitro-pyridin-3-yloxy)acetate

2-Bromo-5-hydroxy-6-nitropyridine (40 g of crude material from Preparation 4(a), 0.14 mole) was suspended in acetone (650 mL) with mechanical stirring, and potassium carbonate (39 g, 0.28 mole) was added, followed by ethyl bromoacetate (19 mL, 0.171 mmole). The reaction was heated at reflux for 10 hr, then was cooled to RT and diluted with water (1 L). The mixture was extracted with ether (700 mL, 2 times). The organic layer was washed sequentially with water and brine, dried (Na$_2$SO$_4$), and concentrated in vacuo to afford the title compound (41 g): MS (ES) m/e 305.0 (M+H)$^+$. This material was >85% pure and was used without further purification. Note: The dibrominated material does not alkylate as fast as the monobrominated material. Thus the dibromohydroxynitropyridine is washed out in the workup.

(c) 6-Bromo-4H-pyrido[3,2-b][1,4]oxazin-3-one

Ammonium chloride (44 g, 0.823 mole) was dissolved in H$_2$O (600 mL), and iron powder (−325 mesh, 27.4 g, 0.491 mole) was added. The mixture was mechanically stirred (vigorously), and a solution of ethyl (6-bromo-2-nitro-pyridin-3-yloxy)acetate (50 g, 0.164 mole) in MeOH (800 mL) was added slowly at RT over 3 hours. When the addition was done, the reaction was heated at reflux for 3 hr and then hot-filtered through a pad of Celite®. The filter pad was washed with hot MeOH (500 mL) and the filtrate was concentrated in vacuo. When most of the MeOH was removed, the mixture was filtered to collect the solid, which was washed with water (100 mL). The filtrate was extracted with CHCl$_3$ (300 mL, 2 times) and the organic layer was washed sequentially with water and brine, dried (MgSO$_4$), and concentrated in vacuo. The residue was combined with the solid from the filtration, suspended in glacial AcOH (150 mL), and the mixture was heated at 95° C. for 3 hr. The mixture was then concentrated in vacuo and the residue was triturated with Et₂O (200 mL). The solid was collected, washed with ether, and dried to afford the title compound (30 g, 80%): MS (ES) m/e 229.0 (M+H)⁺.

(d) 6-((E)-Styryl)-4H-pyrido[3,2-b][1,4]oxazin-3-one

6-Bromo-4H-pyrido[3,2-b][1,4]oxazin-3-one (10.0 g, 44 mmole) and trans-2-phenylvinylboronic acid (9.0 g, 61 mmole) were dissolved in 1,4-dioxane (200 mL) and the solution was degassed with argon. (Ph₃P)₄Pd (2.5 g, 2.2 mmole) was added, followed by a solution of potassium carbonate (15 g, 109 mmole) in H₂O (100 mL). The reaction was heated at reflux under argon overnight, then was cooled to room temperature and diluted with CHCl₃ (400 mL). The solution was washed sequentially with H₂O and brine, dried (Na₂SO₄), and concentrated in vacuo. The solid residue was recrystallized from hot EtOAc to afford the title compound (6.4 g, 57.5%): MS (ES) m/e 253.0 (M+H)⁺.

(e) 3-Oxo-3,4-dihydro-2H-pyrido[3,2-b][1,4]oxazine-6-carboxaldehyde 6-((E)-Styryl)-4H-pyrido[3,2-b][1,4]oxazin-3-one (6.2 g, 27 mmole) was dissolved in 5:1 CH₂Cl₂/MeOH (500 mL) and the solution was cooled to −78° C. Ozone was bubbled through the solution with stirring until a pale blue color appeared, then the excess ozone was removed by bubbling oxygen through the solution for 15 min. Dimethylsulfide (9.9 mL, 135 mmole) was added to the solution, and the reaction was stirred at −78° C. for 3 hr, then at RT overnight. The solvent was removed in vacuo, and the residue was triturated and stirred with Et₂O (150 mL). The solid was collected, washed with additional Et₂O, and dried to afford the title compound (3.4 g, 77%): MS (ES) m/e 179.0 (M+H)⁺.

Preparation 5

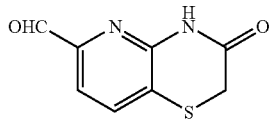

Preparation of 3-oxo-3,4-dihydro-2H-pyrido[3,2-b][1,4]thiazine-6-carboxaldehyde

(a) Methyl 3-oxo-3,4-dihydro-2H-pyrido[3,2-b][1,4]thiazine-6-carboxylate

Sodium hydride (60% dispersion in mineral oil, 540 mg, 13.5 mmole) was added to a solution of ethyl thioglycolate (1.473 mL, 13.43 mmole) in DMF (48 mL) at 0° C. After 1 hr, methyl 6-amino-5-bromopyridine-2-carboxylate (3 g, 13 mmole; prepared by the method of Kelly, T. R.; Lang, F. *J. Org. Chem.* 1996, 61, 4623-4633) was added and the mixture was stirred at RT. After 16 hr, the solution was diluted with EtOAc (1 L), washed with water (3×300 mL), dried and concentrated to about 10 mL. The white solid was collected and washed with a little EtOAc to give the title compound (950 mg, 33%): MS (APCI⁻) m/e 223 (M−H)⁻.

(b) 3-Oxo-3,4-dihydro-2H-pyrido[3,2-b][1,4]thiazine-6-carboxylic acid 0.5 M NaOH solution (8 mL, 4 mmole) was added dropwise over 2 hr to a solution of methyl 3-oxo-3,4-dihydro-2H-pyrido[3,2-b][1,4]thiazine-6-carboxylate (788 mg, 3.52 mmole) in dioxane (120 mL) and water (30 mL). The reaction was stirred overnight then was concentrated to about 3 mL. Water (5 mL) was added and the pH was adjusted to 4 with 2 M HCl. The precipitated solid was collected, washed with a small volume of water and dried under vacuum to give the title compound (636 mg, 86%) as a solid: MS (APCI⁻) m/e 209 (M−H)⁻, 165 (M−COOH)⁻.

(c) 6-Hydroxymethyl-3-oxo-3,4-dihydro-2H-pyrido[3,2-b][1,4]thiazine

A solution of 3-oxo-3,4-dihydro-2H-pyrido[3,2-b][1,4]thiazine-6-carboxylic acid (500 mg, 2.38 mmole) and triethylamine (0.396 mL, 2.84 mmole) in THF (24 mL) was cooled to −10° C. and isobutyl chloroformate (0.339 mL, 2.61 mmole) was added. After 20 min the suspension was filtered through kieselguhr into an ice-cooled solution of sodium borohydride (272 mg, 7.19 mmole) in water (8 mL). The mixture was stirred for 30 min, then the pH was adjusted to 7 with dilute HCl. The solvent was evaporated and the residue was triturated with water. The solid was collected and dried under vacuum to give the title compound (346 mg, 74%) as a white solid: MS (APCI⁻) m/e 197 (M−H)⁻.

(d) 3-Oxo-3,4-dihydro-2H-pyrido[3,2-b][1,4]thiazine-6-carboxaldehyde

A solution of 6-hydroxymethyl-3-oxo-3,4-dihydro-2H-pyrido[3,2-b][1,4]thiazine (330 mg, 1.68 mmole) in CH₂Cl₂ (30 mL) and THF (30 mL) was treated with MnO₂ (730 mg, 8.40 mmole), and the mixture was stirred at RT. Additional MnO₂ was added after 1 hr (730 mg, 8.40 mmole) and after 16 hr (300 mg, 3.45 mmole). After a total of 20 hr the mixture was filtered through kieselguhr and the filtrate was concentrated to dryness. The reside was triturated with 1:1 EtOAc/hexanes, collected, and dried to afford the title compound (180 mg, 55%) as a solid: MS (APCI⁻) m/e 195 (M−H)⁻.

Preparation 6

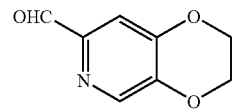

Preparation of 2,3-dihydro[1,4]dioxino[2,3-c]pyridine-7-carbaldehyde

(a) 5-Benzyloxy-2-(hydroxymethyl)-4(1H)-pyridinone

A mixture of 5-benzyloxy-2-hydroxymethyl-4H-pyran-4-one (9.7 g, 42 mmole; prepared from Kojic acid by the method of Erol, D. *J. Med. Chem.* 1994, 29, 893) concentrated aqueous ammonia (100 mL), and ethanol (20 mL) was heated at reflux overnight. The mixture was allowed to cool to RT and the solid was collected, washed with Et₂O and dried in vacuo to afford the title compound (5.9 g, 61%): MS (APCI⁺) m/e 232 (M+H)⁺.

(b) 2,3-Dihydro[1,4]dioxino[2,3-c]pyridin-7-ylmethanol

A solution of 5-benzyloxy-2-(hydroxymethyl)-4(1H)-pyridinone (2 g, 8.7 mmole) and NaOH (680 mg, 17 mmole) in water (220 mL) was hydrogenated over 10% palladium on charcoal (1 g). After 4 hr, the mixture was filtered and the filtrate was concentrated to dryness. The resulting white solid was dissolved in DMF (8 mL) then treated with potassium carbonate (2.9 g, 21 mmole) and 1,2-dibromoethane (0.6 mL, 7 mmole). The mixture was heated at 85° C. overnight. The cooled mixture was concentrated onto silica gel and chromatographed (gradient elution: 10-30% MeOH/EtOAc) to afford the title compound (250 mg, 17%) as a white solid: MS (APCI$^+$) m/e 168 (M+H)$^+$.

(c) 2,3-Dihydro[1,4]dioxino[2,3-c]pyridine-7-carbaldehyde

A solution of 2,3-dihydro[1,4]dioxino[2,3-c]pyridin-7-ylmethanol (250 mg, 1.5 mmole) in CH$_2$Cl$_2$ (5 mL) was treated with MnO$_2$ (650 mg, 7.5 mmole). After 3 days the mixture was filtered and the filtrate was concentrated to afford the title compound (150 mg, 61%) as a white solid: MS (APCI$^+$) m/e 166 (M+H)$^+$.

EXAMPLE 1

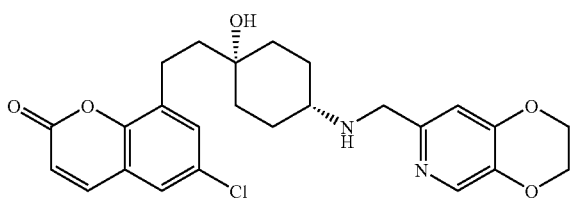

Preparation of 6-chloro-8-(2-{cis-4-[(2,3-dihydro[1,4]dioxino[2,3-c]pyridin-7-ylmethyl)amino]-1-hydroxycyclohexyl}ethyl)-2H-chromen-2-one To a solution of 8-[2-(cis-4-amino-1-hydroxycyclohexyl)ethyl]-6-chloro-2H-chromen-2-one hydrochloride (35 mg, 0.10 mmol), sodium bicarbonate (35 mg, 0.42 mmol), and anhydrous sodium sulfate (85 mg, 0.60 mmol) in 1:1 methanol/CH$_2$Cl$_2$ (2 mL) was added 2,3-dihydro[1,4]dioxino[2,3-c]pyridine-7-carbaldehyde (20 mg, 0.11 mmol). The solution was allowed to stir at RT for 14 h, then sodium borohydride (4 mg, 0.10 mmol) was added. The solution was stirred for an additional 1 h then was concentrated under reduced pressure. Flash chromatography on silica gel (90:9:1 CHCl$_3$/MeOH/conc NH$_4$OH) gave the title compound (31 mg, 66%) as a white solid: $^1$H NMR (400 MHz, DMSO-d$_6$) δ 8.13 (s, 1H), 7.63 (d, J=9.6 Hz, 1H), 7.42-7.25 (m, 2H), 6.85 (m, 1H), 6.46 (d, J=8.0 Hz, 1H), 4.40-4.20 (m, 4H), 3.80 (s, 2H), 2.94-2.78 (m, 2H), 2.75-2.58 (m, 2H), 2.0-1.6 (m, 8H), 1.65-1.30 (m, 3H); MS (ES) m/e 471, 473 (M+H)$^+$.

EXAMPLE 2

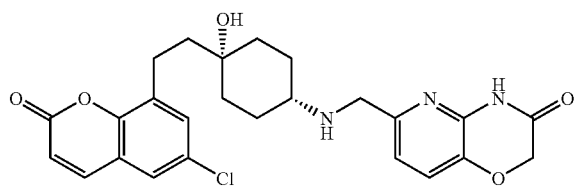

Preparation of 6-[({cis-4-[2-(6-Chloro-2-oxo-2H-chromen-8-yl)ethyl]-4-hydroxycyclohexyl}amino)methyl]-2H-pyrido[3,2-b][1,4]oxazin-3(4H)-one According to the procedure of Example 1, except using 3-oxo-3,4-dihydro-2H-pyrido[3,2-b][1,4]oxazine-6-carbaldehyde in place of the 2,3-dihydro[1,4]dioxino[2,3-c]pyridine-7-carbaldehyde, the title compound (40 mg, 83%) was prepared as a tan solid: $^1$H NMR (400 MHz, DMSO-d$_6$) δ 7.63 (d, J=8.0 Hz, 1H), 7.39 (s, 1H), 7.32-7.22 (m, 2H), 7.02 (m, 1H), 6.46 (d, J=8.0 Hz, 1H), 4.70-4.55 (m, 4H), 4.01 (s, 1H), 2.94-2.78 (m, 2H), 2.75-2.68 (m, 1H), 2.0-1.6 (m, 7H), 1.65-1.30 (m, 3H); MS (ES) m/e 484, 486 (M+H)$^+$.

EXAMPLE 3

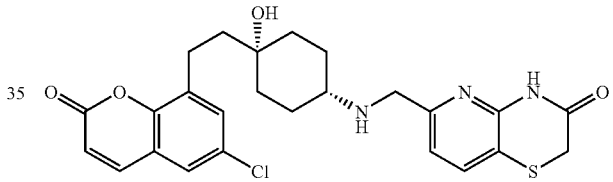

Preparation of 6-[({cis-4-[2-(6-chloro-2-oxo-2H-chromen-8-yl)ethyl]-4-hydroxycyclohexyl}amino)methyl]-2H-pyrido[3,2-b][1,4]thiazin-3(4H)-one According to the procedure of Example 1, except using 3-oxo-3,4-dihydro-2H-pyrido[3,2-b][1,4]thiazine-6-carbaldehyde in place of the 2,3-dihydro[1,4]dioxino[2,3-c]pyridine-7-carbaldehyde, the title compound (14 mg, 27%) was prepared as a yellow solid: $^1$H NMR (400 MHz, DMSO-d$_6$) δ 7.65 (d, J=9.6 Hz, 1H), 7.57 (d, J=7.6 Hz, 1H), 7.39 (s, 1H), 7.32 (s, 1H), 6.93 (d, J=7.6 Hz, 1H), 6.44 (d, J=9.6 Hz, 1H), 3.83 (s, 1H), 3.54-3.32 (m, 4H), 2.95-2.88 (m, 2H), 1.85-1.5 (m, 7H), 1.45-1.20 (m, 3H); MS (ES) m/e 500, 502 (M+H)$^+$.

EXAMPLE 4

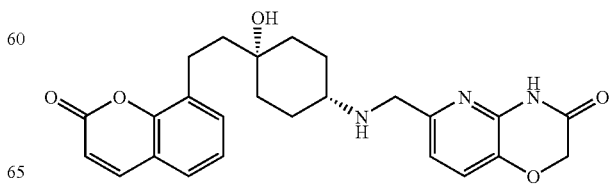

Preparation of 6-[({cis-4-hydroxy-4-[2-(2-oxo-2H-chromen-8-yl)ethyl]cyclohexyl}amino)methyl]-2H-pyrido[3,2-b][1,4]oxazin-3(4H)-one A solution of 8-[2-(cis-4-amino-1-hydroxycyclohexyl)ethyl]-2H-chromen-2-one, hydrochloride (61.7 mg, 0.172 mmol) and NaHCO₃ (36 mg, 0.43 mmol) was stirred in MeOH (1.0 mL) at RT for 5 min. Dichloromethane (1.0 mL), 3-oxo-3,4-dihydro-2H-pyrido[3,2-b][1,4]oxazine-6-carbaldehyde (32.1 mg, 0.18 mmol), and Na₂SO₄ (193 mg, 1.36 mmol) were added and the reaction was stirred at RT for 18 h. The intermediate imine was treated with sodium triacetoxyborohydride (47 mg, 0.213 mmol) and the mixture was stirred for an additional 16 h. The reaction was acidified (pH 3) with 6 N HCl and stirred for 10 min, then the solvents were removed under reduced pressure. The residue was partitioned between dichloromethane and aqueous sodium bicarbonate, the layers were separated, and the organic layer was dried (Na₂SO₄). Purification by column chromatography using the ISCO Companion (Redi-Sep™ silica gel column, gradient 1% to 20% MeOH/CH₂Cl₂) yielded the title compound (31.2 mg, 40%) as an amorphous yellow solid: ¹H NMR (400 MHz, CDCl₃) δ 7.71 (d, J=9.5 Hz, 1H), 7.43 (d, J=7.1 Hz, 1H), 7.32 (d, J=7.4 Hz, 1H), 7.18-7.28 (m, 2H), 6.99 (d, J=7.7 Hz, 1H), 6.41 (d, J=9.5 Hz, 1H), 4.65 (s, 2H), 4.01 (bs, 2H), 2.97 (bt, J=8.2 Hz, 2H), 2.86-2.89 (m, 2H), 2.65-2.76 (m, 1H), 1.96-2.04 (m, 6H), 1.79-1.83 (m, 2H), 1.41-1.49, (m, 2H); MS (ES) m/e 450.2 (M+H)⁺.

EXAMPLE 5

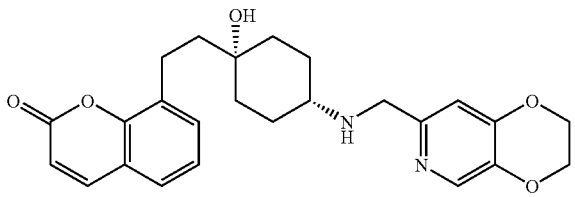

Preparation of 8-(2-{cis-4-[(2,3-dihydro[1,4]dioxino[2,3-c]pyridin-7-ylmethyl)amino]-1-hydroxycyclohexyl}ethyl)-2H-chromen-2-one According to the procedure of Example 4, except using 2,3-dihydro[1,4]dioxino[2,3-c]pyridine-7-carbaldehyde in place of the 3-oxo-3,4-dihydro-2H-pyrido[3,2-b][1,4]oxazine-6-carbaldehyde, the title compound (28.9, 39%) was prepared as an amorphous light yellow solid: ¹H NMR (400 MHz, CDCl₃) δ 8.12 (s, 1H), 7.71 (d, J=9.5 Hz, 1H), 7.43 (d, J=7.2 Hz, 1H), 7.33 (d, J=7.1 Hz, 1H), 7.19-7.23 (m, 1H), 6.93 (s, 1H), 6.42 (d, J=9.5 Hz, 1H), 4.33 (dd, J=12.6 Hz, J=4 Hz, 4H), 3.96 (s, 2H), 3.10 (bs, 1H), 2.90-2.99 (m, 3H), 2.64-2.76 (m, 2H), 1.67-1.94 (m, 7H), 1.48 (bt, J=11.7, 2H); MS (ES) m/e 437.4 (M+H)⁺.

Preparation 7

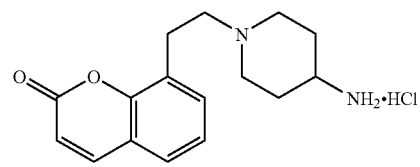

Preparation of 8-[2-(4-amino-1-piperidinyl)ethyl]-2H-chromen-2-one hydrochloride (a) 8-(2-propen-1-yl)-2H-chromen-2-one To a solution of 3-allylsalicylaldehyde (1.62 g, 10.0 mmol) in acetic anhydride (2 mL) in a 5 mL Emrys process vial was added Et₃N (2.0 ml). The reaction was heated at 160° C. for 45 min in an Emrys Optimizer Microwave reactor then was cooled to RT. The reaction was diluted with 50 mL of ethyl acetate, the organic layer was washed with aqueous ammonium chloride, aqueous sodium chloride, dried (Na₂SO₄), and concentrated. Purification of the residue by flash chromatography on silica gel (gradient elution: 5% to 30% Ethyl acetate/Hexanes) yielded the title compound (750 mg, 40%) as a colorless oil: MS (ES) m/e 186.9 (M+H)⁺.

(b) (2-oxo-2H-chromen-8-yl)acetaldehyde

To a solution of 8-(2-propen-1-yl)-2H-chromen-2-one (390 mg, 2.0 mmol) in dioxane (10 mL) and water (5 mL) was added OsO₄ (4% solution in H₂O, 0.5 mL, 10 mol %) and NaIO₄ (430 mg, 4.0 mmol). The reaction was stirred at RT for 2 h and NaIO₄ (430 mg, 4.0 mmol) was added and the reaction was allowed to stir another 2 h. The reaction was diluted with 20 mL of H₂O and was extracted with ethyl acetate (3×50 mL). The combined extracts were dried (Na₂SO₄), and concentrated to give the title compound (350 mg, 93%) as a dark oil which was used without further purification: MS (ES) m/e 188.9 (M+H)⁺.

(c) (1,1-dimethylethyl {1-[2-(2-oxo-2H-chromen-8-yl)ethyl]-4-piperidinyl}carbamate To a solution of (2-oxo-2H-chromen-8-yl)acetaldehyde (190 mg, 1.0 mmol) in 10% MeOH/CH₂Cl₂ (10 mL) was added 4-N—BOC aminopiperidine (200 mg, 1.0 mmol). The reaction was allowed to stir for 2 h and Na (and NaIO₄ (430 mg, 4.0 mmol). The reaction was stirred at RT for 2 h and NaBH(OAc)₃ (420 mg, 2.0 mmol) was added. The reaction was allowed to stir for 14 h. The reaction was absorbed onto silica gel and purified by flash chromatography 0 to 10% MeOH/CH₂Cl₂) yielded the title compound (320 mg, 86%) as an off-white solid: MS (ES) m/e 373.0 (M+H)⁺.

(d) 8-[2-(4-amino-1-piperidinyl)ethyl]-2H-chromen-2-one hydrochloride

To a solution of (1,1-dimethylethyl {1-[2-(2-oxo-2H-chromen-8-yl)ethyl]-4-piperidinyl}carbamate (320 mg, 0.86 mmol) in 20% MeOH/CH₂Cl₂ (5 mL) at 0° C. was added a solution of HCl in dioxane (4 M, 1.0 mL). The reaction was warmed to RT and stirred for 16 h, then the solvents were removed under reduced pressure to afford the title compound (170 mg, 73%) as a pale yellow solid: MS (ES) m/e 273.0 (M+H)+.

EXAMPLE 6

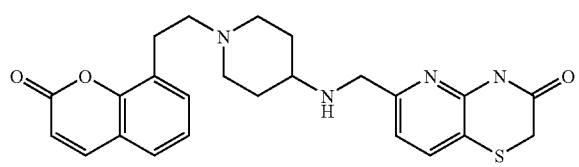

Preparation of 6-[({1-[2-(2-oxo-2H-chromen-8-yl)ethyl]-4-piperidinyl}amino)methyl]-2H-Pyrido[3,2-b][1,4]thiazin-3(4H)-one To a solution of 8-[2-(4-amino-1-piperidinyl)ethyl]-2H-chromen-2-one hydrochloride (41 mg, 0.15 mmol), Et$_3$N (0.10 mL), in 10% methanol/CH$_2$Cl$_2$ (5 mL) was added 3-oxo-3,4-dihydro-2H-pyrido[3,2-b][1,4]thiazine-6-carboxaldehyde (32 mg, 0.17 mmol). The solution was allowed to stir at RT for 16 h, then sodium borohydride (7 mg, 0.17 mmol) was added. The solution was stirred for an additional 30 min then was concentrated under reduced pressure. Flash chromatography on silica gel (90:9:1 CHCl$_3$/MeOH/conc NH$_4$OH) gave the title compound (34 mg, 51%) as a yellow solid: $^1$H NMR (400 MHz, DMSO-d$_6$) δ 7.99 (d, J=9.6 Hz, 1H), 7.79 (d, J=7.8 Hz, 1H), 7.50-7.62 (m, 2H), 7.32 (m, 1H), 7.11 (d, J=7.8 Hz, 1H), 6.47 (d, J=9.6 Hz, 1H), 4.17 (s, 2H), 3.57 (s, 2H), 3.36-3.04 (m, 5H), 3.00-2.84 (m, 2H), 2.62-2.38 (m, 2H), 2.33-2.10 (m, 2H), 1.87-1.62 (m, 2H); MS (ES) m/e 451.1 (M+H)+.

EXAMPLE 7

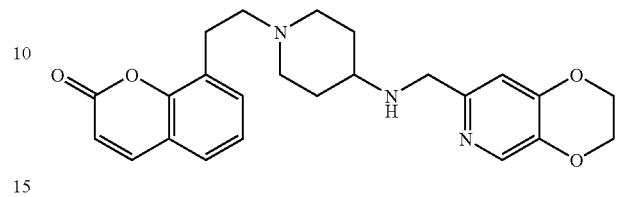

Preparation of 8-(2-{4-[(2,3-dihydro[1,4]dioxino[2,3-c]pyridin-7-ylmethyl)amino]-1-piperidinyl}ethyl)-2H-chromen-2-one According to the procedure of Example 6, except using 2,3-dihydro[1,4]dioxino[2,3-c]pyridine-7-carbaldehyde (see, e.g., WO2004058144; especially WO2003087098) in place of the 3-oxo-3,4-dihydro-2H-pyrido[3,2-b][1,4]thiazine-6-carboxaldehyde, the title compound (35 mg, 55%) was prepared as a tan solid: $^1$H NMR (400 MHz, DMSO-d$_6$) δ 8.11 (s, 1H), 7.98 (d, J=9.6 Hz, 1H), 7.66-7.45 (m, 2H), 7.40-7.21 (m, 1H), 7.04 (s, 1H), 6.46 (d, J=9.6 Hz, 1H), 4.49-4.26 (m, 4H), 4.13 (s, 2H), 3.48-3.20 (m, 5H), 3.03-2.81 (m, 2H), 2.72-2.46 (m, 2H), 2.31-2.13 (m, 2H), 1.90-1.69 (m, 2H); MS (ES) m/e 422.0 (M+H)+.

TABLE OF EXAMPLES 1-7

| Example # | Structure | Formula |
| --- | --- | --- |
| 1 | 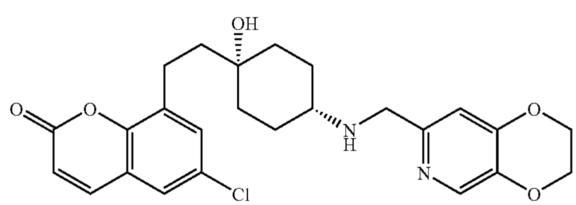 | 6-chloro-8-(2-{cis-4-[(2,3-dihydro[1,4]dioxino[2,3-c]pyridin-7-ylmethyl)amino]-1-hydroxycyclohexyl}ethyl)-2H-chromen-2-one |
| 2 | 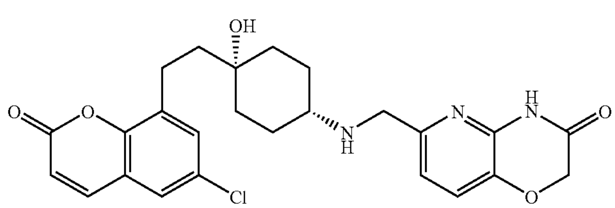 | 6-[({cis-4-[2-(6-Chloro-2-oxo-2H-chromen-8-yl)ethyl]-4-hydroxycyclohexyl}amino)methyl]-2H-pyrido[3,2-b][1,4]oxazin-3(4H)-one |
| 3 | 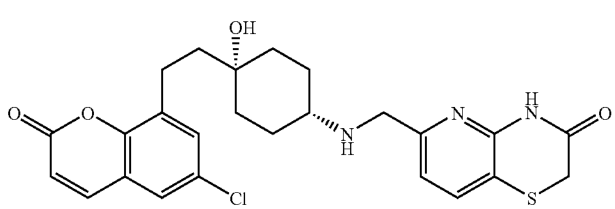 | 6-[({cis-4-[2-(6-chloro-2-oxo-2H-chromen-8-yl)ethyl]-4-hydroxycyclohexyl}amino)methyl]-2H-pyrido[3,2-b][1,4]thiazin-3(4H)-one |

-continued

| Example # | Structure | Formula |
|---|---|---|
| 4 | 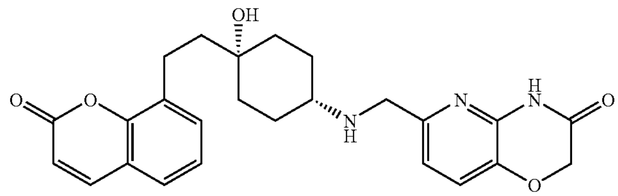 | 6-[({cis-4-hydroxy-4-[2-(2-oxo-2H-chromen-8-yl)ethyl]cyclohexyl}amino)methyl]-2H-pyrido[3,2-b][1,4]oxazin-3(4H)-one |
| 5 | 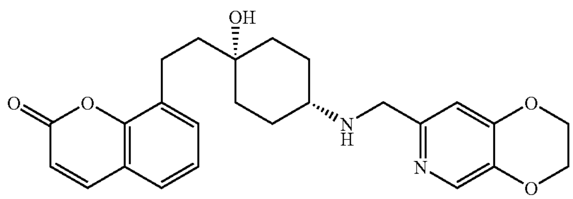 | 8-(2-{cis-4-[(2,3-dihydro[1,4]dioxino[2,3-c]pyridin-7-ylmethyl)amino]-1-hydroxycyclohexyl}ethyl)-2H-chromen-2-one |
| 6 | 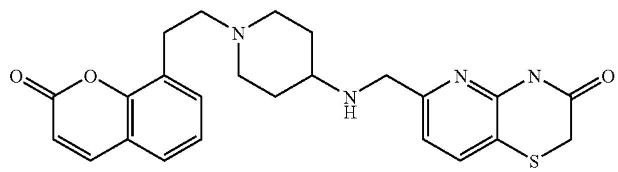 | 6-[({1-[2-(2-oxo-2H-chromen-8-yl)ethyl]-4-piperidinyl}amino)methyl]-2H-pyrido[3,2-b][1,4]thiazin-3(4H)-one |
| 7 | 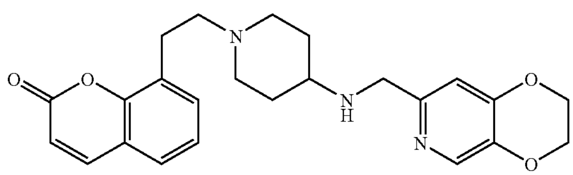 | 8-(2-{4-[(2,3-dihydro[1,4]dioxino[2,3-c]pyridin-7-ylmethyl)amino]-1-piperidinyl}ethyl)-2H-chromen-2-one |

EXAMPLE 8

Antimicrobial Activity Assay

Unless otherwise stated, whole-cell antimicrobial activity was determined by broth microdilution using the National Committee for Clinical Laboratory Standards (NCCLS) recommended procedure, Document M7-A6, "Methods for Dilution Susceptibility Tests for Bacteria that Grow Aerobically". Also unless otherwise stated, the compounds were tested in serial two-fold dilutions ranging from 0.016 to 16 mcg/mL.

Compounds were evaluated against a panel of Gram-positive organisms, including *Staphylococcus aureus, Streptococcus pneumoniae, Streptococcus pyogenes, Enterococcus faecalis* and *Enterococcus faecium.*

In addition, compounds were evaluated against a panel of Gram-negative strains including *Haemophilus influenzae, Moraxella catarrhalis, Escherichia coli, Pseudomonas aeruginosa, Proteus mirabilis, Legionella pneumophila, Chlamydia pneumoniae, Enterobacter cloacae, Enterobacter aerogenes, Klebsiella pneumoniae* and *Stenotrophomonas maltophilia.*

The *L. pneumophila* isolates were tested using a modified CLSI procedure for broth microdilution. For this assay, compounds were tested in serial doubling dilutions over a concentration range of 0.03 to 32 mcg/mL. An inoculum of each test isolate was prepared in buffered yeast broth and adjusted to a density equivalent to a 0.5 McFarland standard. After inoculation, the microtitre plates were incubated at 37° C. for 72 hours. The MIC was determined as the minimum concentration of drug that inhibited visible growth of the test isolate.

For the *C. pneumoniae* isolates, stocks were thawed and diluted in CCM to yield an inoculum containing ~1×10$^4$ inclusion forming units/ml (IFUs/ml). A 100 μL aliquot of the inoculum was added to all wells of a microtitre plate containing HEp-2 cells grown to confluence. Microtitre plates were centrifuged for 1 hour at 1700 g., then incubated for 1 hour at 35° C. in 5% $CO_2$. One hundred microliters of diluted test compounds, prepared as a 2-fold dilution series in CCM/cycloheximide was then added to the microtiter plates. After 72 hours incubation at 35° C. in 5% $CO_2$, the microtitre plates were stained with a murine monoclonal fluorescein-conjugated antibody (Kallestad Cat. #532 Roche Biomedical Products) in accordance with the manufacturer recommendations. Upon staining, the IFUs produced an apple-green color, visible against the red counter stained HEp-2 cells when viewed at 100× magnification. The MIC was defined as the lowest concentration of compound at which no IFUs were seen.

Unless otherwise stated, the minimum inhibitory concentration (MIC) was determined as the lowest concentration of compound that inhibited visible growth. A mirror reader was used to assist in determining the MIC endpoint.

One skilled in the art would consider any compound with a MIC of less than 20 mg/mL to be a potential lead compound. For instance, each of the listed Examples (1 through 7), as identified in the present application, had a MIC≦20 mg/ml against at least one of the organisms listed above.

It is to be understood that the invention is not limited to the embodiments illustrated hereinabove and the right is reserved to the illustrated embodiments and all modifications coming within the scope of the following claims.

What is claimed is:

1. A compound of formula (I) or a pharmaceutically acceptable salt thereof:

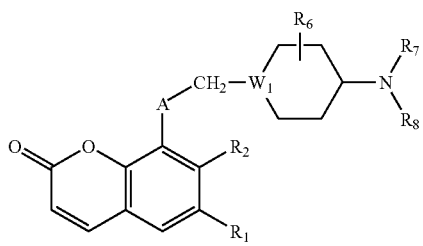

wherein:
$R_1$ is hydrogen; fluorine; or chlorine;
$R_2$ is hydrogen; fluorine; chlorine; or CN;
A is $CR_3R_4$;
$R_3$ is hydrogen;
$R_4$ is hydrogen or hydroxyl;
$W_1$ is $CR_5$ or N;
$R_5$ is hydrogen or hydroxyl;
$R_6$ is hydrogen, $(C_{1-6})$alkyl; fluorine; chlorine; $NR^{1a}R^{1a'}$; $(C_{1-6})$alkyl$NR^{1a}R^{1a'}$; $(C_{1-6})$alkoxy; $(C_{1-6})$alkyl$(C_{1-6})$alkoxy; $(C_{1-6})$hydroxyalkyl; hydroxyl; aryl; heteroaryl; heterocyclyl; $(C_{1-6})$aralkyl; thiol; $(C_{1-6})$alkylthio; $C(=O)NR^{1a}R^{1a'}$; $(C_{1-6})$alkyl$C(=O)NR^{1a}R^{1a'}$; $C(=O)R^{1b}$; $(C_{1-6})$alkyl$C(=O)R^{1b}$; $CO_2R^{1b}$; or $(C_{1-6})$alkyl$CO_2R^{1b}$;
each $R^{1a}$ and $R^{1a'}$ are independently hydrogen; acyl; $(C_{1-6})$alkyl; aryl; heteroaryl; or together with the nitrogen they are attached form an aziridine, azetidine, pyrrolidine, piperidine or hexamethyleneimine ring (wherein said aziridine, azetidine, pyrrolidine, piperidine or hexamethyleneimine ring is optionally substituted with 1 to 3 substitutents selected from halogen, $(C_{1-6})$alkyl, hydroxyl or aryl);
each $R^{1b}$ is independently hydrogen; $(C_{1-6})$alkyl; aryl; or heteroaryl;
$R_7$ is hydrogen; $(C_{1-6})$alkyl$(C_{1-6})$alkoxy; $(C_{1-6})$alkyl$NR^{1a}R^{1a'}$; or $(C_{1-6})$alkyl;
$R_8$ is represented by the following structure:

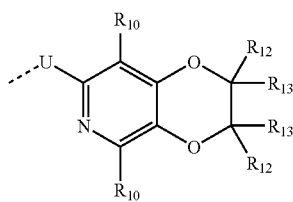

$R_{10}$, $R_{12}$ and $R_{13}$ are at each occurrence independently selected from the group consisting of: H; $(C_{1-4})$alkylthio; halo; $(C_{1-4})$alkyl; $(C_{2-4})$alkenyl; hydroxy; hydroxy$(C_{1-4})$alkyl; mercapto$(C_{1-4})$alkyl; $(C_{1-4})$alkoxy; trifluoromethoxy; nitro; cyano; carboxy; and amino or aminocarbonyl unsubstituted or substituted by $(C_{1-4})$alkyl;
and where U is $C(=O)$; $SO_2$; or $CH_2$;
"acyl" is $C(=O)$ $(C_{1-13})$alkyl or $C(=O)$aryl; and
"aryl" is optionally substituted phenyl or naphthyl.

2. A compound according to claim 1, wherein $R_1$ is hydrogen.

3. A compound according to claim 1, wherein $R_1$ is chlorine.

4. A compound according to claim 1, wherein $R_2$ is hydrogen or fluorine.

5. A compound according to claim 1, wherein A is $CH_2$.

6. A compound according to claim 1, wherein $W_1$ is $CR_5$.

7. A compound according to claim 1, wherein $W_1$ is N.

8. A compound according to claim 1, wherein $R_5$ is hydroxyl.

9. A compound according to claim 1, wherein $R_6$ is hydrogen.

10. A compound according to claim 1, wherein $R_7$ is hydrogen.

11. A compound according to claim 1, wherein U is $CH_2$.

12. A compound according to claim 1, selected from the group consisting of:
8-(2-{cis-4-[(2,3-dihydro[1,4]dioxino[2,3-c]pyridin-7-ylmethyl)amino]-1-hydroxycyclohexyl}ethyl)-2H-chromen-2-one;
8-(2-{4-[(2,3-dihydro[1,4]dioxino[2,3-c]pyridin-7-ylmethyl)amino]-1-piperidinyl}ethyl)-2H-chromen-2-one;
or a pharmaceutically acceptable salt thereof.

13. A compound of claim 1 which is a pharmaceutically acceptable salt of a compound of formula (I).

14. A pharmaceutical composition comprising a compound according to claim 1 and a pharmaceutically acceptable carrier.

15. A method of treating a bacterial infection in a mammal due to an organism selected from *Staphylococcus aureus, Streptococcus pneumoniae, Streptococcus pyogenes, Enterococcus faecalis, Enterococcus faecium, Haemophilus influenza, Escherichia Coli, Pseudomonas aeruginosa, Proteus mirabilis, Legionella pneumophila, Chlamydia pneumoniae, Enterobacter cloacae, Enterobacter aerogenes, Klebsiella pneumoniae, Stenotrophomonas maltophilia* and *Moraxella catarrhalis*, which comprises administering to a mammal in need thereof an effective amount of the compound according to claim 1.

16. A compound according to claim 1 wherein:
$R_1$ is hydrogen or chlorine;
$R_2$ is hydrogen or fluorine;
A is $CH_2$;
$W_1$ is $CR_5$;
$R_5$ is hydroxyl;
$R_6$ is hydrogen;
$R_7$ is hydrogen; and
U is $CH_2$.

17. A compound according to claim 1 wherein:
$R_1$ is hydrogen or chlorine;
$R_2$ is hydrogen or fluorine;
A is $CH_2$;
$W_1$ is N;
$R_6$ is hydrogen;
$R_7$ is hydrogen; and
U is $CH_2$.

* * * * *